(12) United States Patent
Ito

(10) Patent No.: US 10,232,364 B2
(45) Date of Patent: Mar. 19, 2019

(54) ASPIRATION TIP

(71) Applicant: YAMAHA HATSUDOKI KABUSHIKI KAISHA, Shizuoka-ken (JP)

(72) Inventor: Saburo Ito, Shizuoka (JP)

(73) Assignee: YAMAHA HATSUDOKI KABUSHIKI KAISHA, Shizuoka-ken (JP)

(*) Notice: Subject to any disclaimer, the term of this patent is extended or adjusted under 35 U.S.C. 154(b) by 58 days.

(21) Appl. No.: 15/038,883

(22) PCT Filed: Nov. 29, 2013

(86) PCT No.: PCT/JP2013/007019
§ 371 (c)(1),
(2) Date: May 24, 2016

(87) PCT Pub. No.: WO2015/079476
PCT Pub. Date: Jun. 4, 2015

(65) Prior Publication Data
US 2017/0001190 A1    Jan. 5, 2017

(51) Int. Cl.
*B01L 3/02* (2006.01)
*C12M 1/26* (2006.01)

(52) U.S. Cl.
CPC .......... *B01L 3/0275* (2013.01); *B01L 3/022* (2013.01); *C12M 33/04* (2013.01);
(Continued)

(58) Field of Classification Search
USPC ..................... 422/501, 524, 525, 921, 923
See application file for complete search history.

(56) References Cited

U.S. PATENT DOCUMENTS 3,641,823 A * 2/1972 Harris, Sr. ........ A61M 5/31531
422/562
3,923,207 A * 12/1975 Kyogoku .............. A61M 5/315
222/386
(Continued)

FOREIGN PATENT DOCUMENTS

JP    S50-084085 U    7/1975
JP    S58-084049 A    5/1983
(Continued)

OTHER PUBLICATIONS

The extended European search report issued by the European Patent Office dated Nov. 23, 2016, which corresponds to European Patent Application No. 13898262.4-1371 and is related to U.S. Appl. No. 15/038,883.

(Continued)

*Primary Examiner* — Dean Kwak
(74) *Attorney, Agent, or Firm* — Studebaker & Brackett PC

(57) ABSTRACT

An aspiration tip is provided with: a syringe section including an inner tubular passage defining an aspiration path for aspirating an object; and a plunger movable in the tubular passage while coming in contact with an inner wall surface of the tubular passage. The syringe section includes an aspiration opening formed in a distal end of the tubular passage for aspirating the object, and the plunger includes a plunger leading end portion configured to protrude from the aspiration opening before the aspiration of the object and at the time of discharge of the object, and retract in the syringe section at the time of the aspiration of the object.

8 Claims, 11 Drawing Sheets

(52) U.S. Cl.
CPC ............... *B01L 2200/0647* (2013.01); *B01L 2300/0832* (2013.01); *B01L 2400/049* (2013.01); *B01L 2400/0478* (2013.01)

(56) References Cited

U.S. PATENT DOCUMENTS

| | | | |
|---|---|---|---|
| 4,474,071 A | 10/1984 | Marteau D'Autry | |
| 5,223,225 A * | 6/1993 | Gautsch | B01L 3/0275 422/516 |
| 5,770,160 A * | 6/1998 | Smith | B01L 3/0217 422/525 |
| 6,589,791 B1 | 7/2003 | LaBudde et al. | |
| 8,163,256 B2 * | 4/2012 | Cote | B01L 3/0279 422/525 |
| 2002/0037239 A1 | 3/2002 | Komatsu | |
| 2002/0164272 A1* | 11/2002 | Harris | B01L 99/00 73/864.44 |
| 2005/0056713 A1 | 3/2005 | Tisone et al. | |
| 2007/0292314 A1 | 12/2007 | Effenhauser et al. | |
| 2012/0230885 A1 | 9/2012 | Korner et al. | |
| 2013/0183212 A1 | 7/2013 | Effenhauser et al. | |
| 2014/0370589 A1 | 12/2014 | Ito | |

FOREIGN PATENT DOCUMENTS

| | | |
|---|---|---|
| JP | 2000-074929 A | 3/2000 |
| JP | 2002-098706 A | 4/2002 |
| JP | 2006-349502 A | 12/2006 |
| JP | 2008-520978 A | 6/2008 |
| WO | 2013/041505 A1 | 3/2013 |
| WO | 2013/108296 A1 | 7/2013 |

OTHER PUBLICATIONS

International Search Report issued in PCT/JP2013/007019; dated Feb. 25, 2014.

* cited by examiner

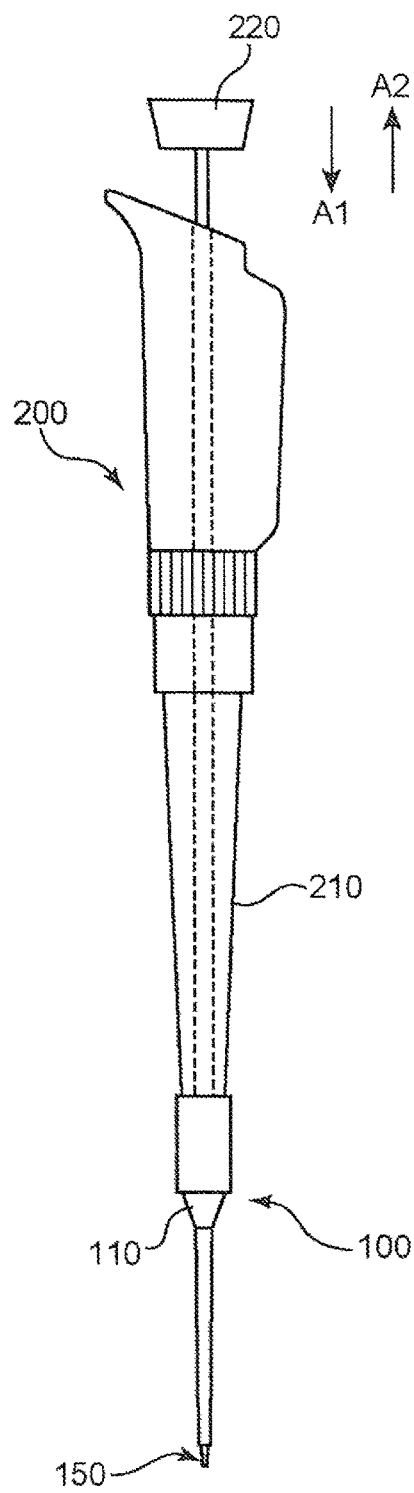

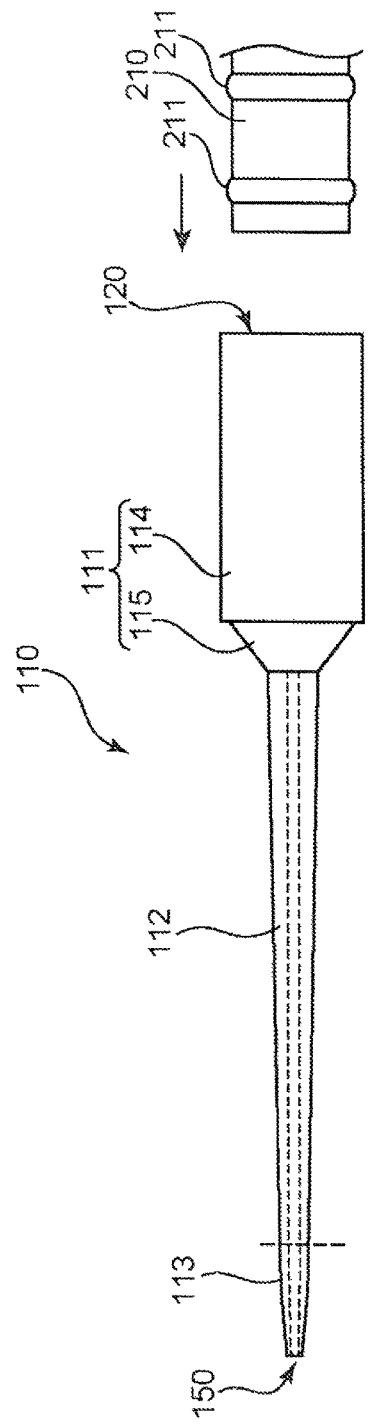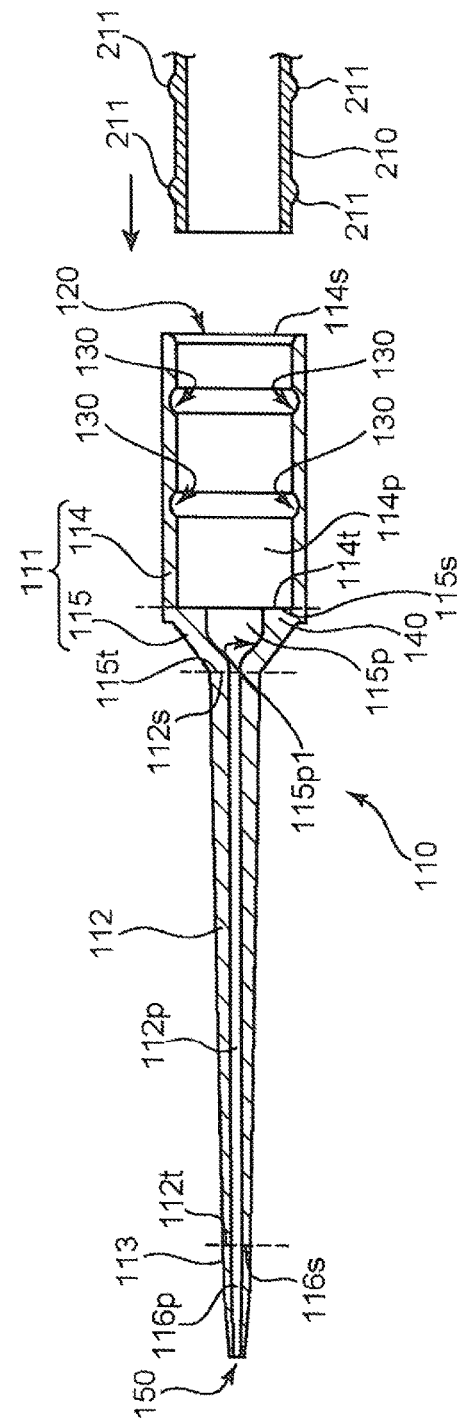
FIG. 3A
FIG. 3B

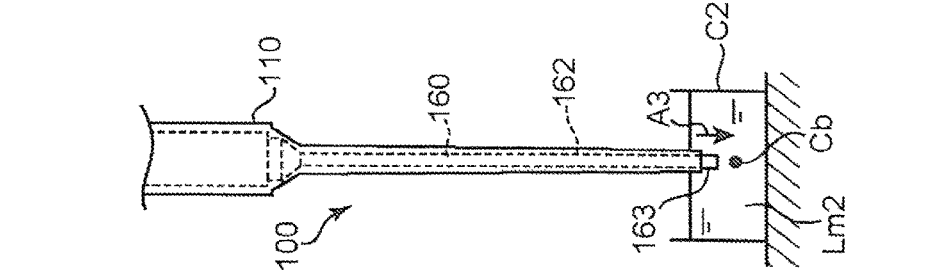
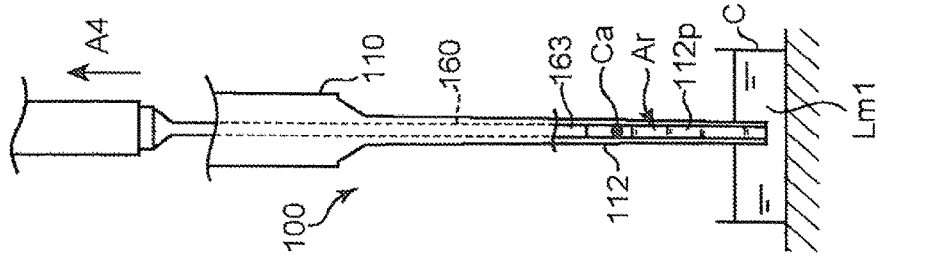
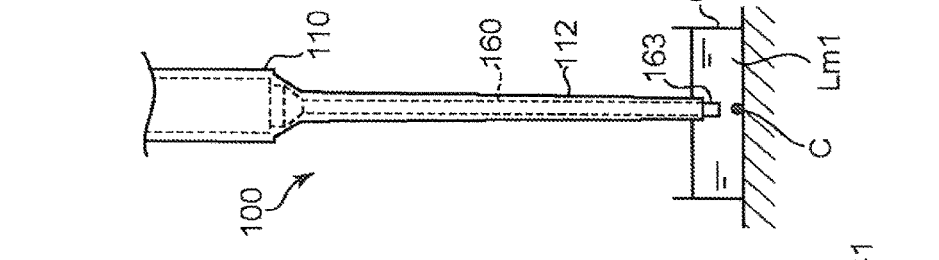
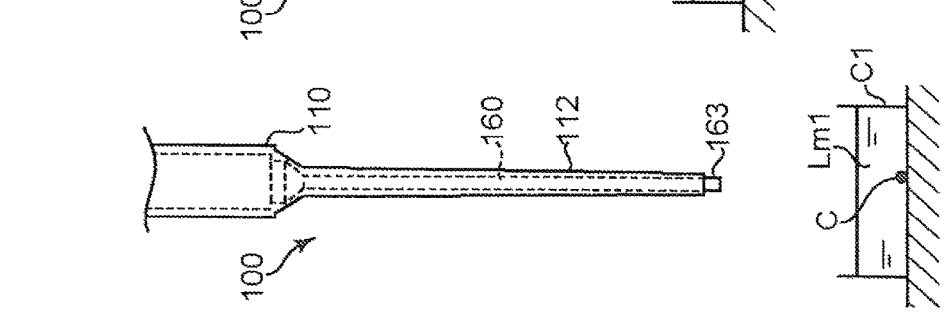
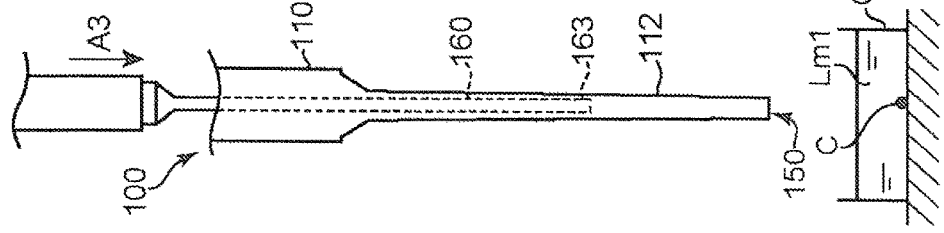

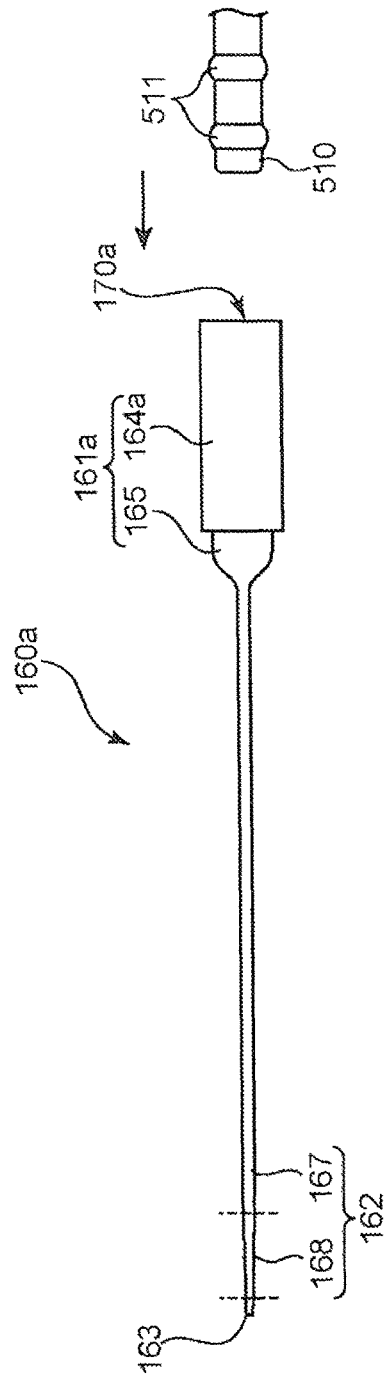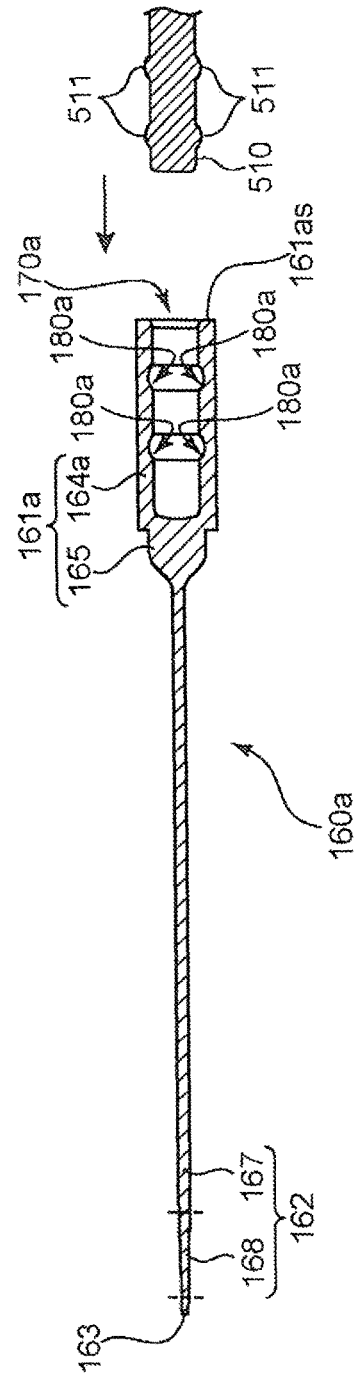
FIG. 10A
FIG. 10B

ASPIRATION TIP

CROSS REFERENCE TO RELATED APPLICATION

This application claims benefit of priority to International Patent Application No. PCT/JP2013/007019 filed Nov. 29, 2013, the entire content of which is incorporated herein by reference.

TECHNICAL FIELD

The present disclosure relates to an aspiration tip capable of aspirating and discharging an accurate amount of an object such as liquid.

BACKGROUND

Conventionally, in a variety of fields, aspiration apparatuses are used for aspirating and measuring a specific volume of an object such as liquid. In particular, an aspiration apparatus is frequently used with an aspiration tip connected to a leading end thereof in, for example, biochemical experiments (Japanese Unexamined Patent Publication No. 2002-98706). The aspiration tip is used as a jig and including a main body portion which is substantially in the form of a cylinder having a tubular passage defining an aspiration path for aspirating an object, one end of the tubular passage being formed with an aspiration opening for aspirating liquid or the like. Another opening is formed in the other end of the aspiration tip to which a nozzle section of the aspiration apparatus for generating an aspiration force is attached.

Examples of the object include not only liquids, but also powder, particles, or biological cells included in a liquid. In the case that the object is a cell, it is possible, by selecting cells based on their shapes by operating the aspiration apparatus to which the aspiration tip is connected, to reduce the deviation of experimental conditions in a variety of experiments that are to be performed using the selected cells. The selected cells can be used for high-throughput screening (HTS), for example.

By the way, the conventional aspiration tip generates a discharging force in the tubular passage of the aspiration tip before the aspiration to preliminarily discharge part of air and, thereafter, a pump mechanism is driven to generate an aspiration force in the tubular passage to aspirate the object, with the aspiration opening being in proximity to or in contact with the object. At the time of discharge, a discharging force is generated in the tubular passage again to discharge the object with air. Thus, the conventional aspiration tip aspirates and discharges the object due to pressure fluctuations inevitable to movements of air in the tubular passage.

In recent years, a technique for accurately aspirating and discharging a very small amount of an object has been required. However, in the case of using the conventional aspiration tip, there is a problem that it is difficult to aspirate and discharge a very small amount of an object efficiently and accurately because volume fluctuations occur owing to contraction and expansion of air or the like in the tubular passage at the time of the aspiration and the discharge. Specifically, for example, in the case that a liquid having a high viscosity is aspirated or discharged, the air in the tubular passage expands or contracts, so that the aspiration speed or the discharge speed (i.e. response to the operation for aspiration or discharge) is liable to decrease, which results in a low working efficiency. Further, in the case that a liquid having a high viscosity, a cell culture solution including impurities or the like is discharged, a portion of the liquid is liable to adhere to and remain on the inner wall surface. In this case, the object is not completely discharged, so that it cannot be measured accurately. Further, in the case that the aspiration tip is used repeatedly with a part of the object remaining in the tubular passage, sample contamination is liable to occur between the samples that have been successively taken. In addition, when the object is observed with an observation device such as a microscope while the object is held in the aspiration tip, for example, the air in the tubular passage may reduce the observation accuracy.

SUMMARY

The present disclosure has been made in view of these problems of the conventional aspiration tip, and aims to provide an aspiration tip capable of aspirating and discharging an object efficiently and accurately by eliminating the influence of air at the time of the aspiration and the discharge.

An aspiration tip according to an aspect of the present disclosure comprises: a syringe section including an inner tubular passage defining an aspiration path for aspirating an object; and a plunger movable in the tubular passage while coming in contact with an inner wall surface of the tubular passage, wherein the syringe section includes an aspiration opening formed in a distal end of the tubular passage for aspirating the object, and the plunger includes a plunger leading end portion configured to protrude from the aspiration opening before the aspiration of the object and at the time of discharge of the object, and retract in the syringe section at the time of the aspiration of the object.

The objects, features and advantages of the present disclosure will become more apparent upon reading the following detailed description along with the accompanying drawings.

BRIEF DESCRIPTION OF DRAWINGS

FIG. 2 is a schematic view of an aspiration pipet attached with the aspiration tip according to the first embodiment of the present disclosure.

FIGS. 3A and 3B are schematic views illustrating a configuration of a syringe section according to the first embodiment of the present disclosure, FIG. 3A being a side view of the syringe section, and FIG. 3B being a sectional view of the syringe section.

FIGS. 7A to 7E are schematic views illustrating an operation of aspirating and discharging a cell aggregation using the aspiration tip according to the first embodiment of the present disclosure, FIG. 7A being a schematic view illustrating a state that the plunger leading end portion is retracted in the syringe section before the aspiration, FIG. 7B being a schematic view illustrating a state that the plunger leading end portion protrudes from an aspiration opening before the aspiration, FIG. 7C being a schematic view illustrating a state that the aspiration opening has approached the cell aggregation, FIG. 7D being a schematic view illustrating a state that the cell aggregation is being aspirated, and FIG. 7E being a schematic view illustrating a state that the cell aggregation is being discharged.

FIGS. 10A and 10B are schematic views illustrating a configuration of a plunger of the aspiration tip according to the second embodiment of the present disclosure, FIG. 10A being a side view of the plunger, and FIG. 10B being a sectional view of the plunger.

DETAILED DESCRIPTION (First Embodiment)
<Aspiration Tip>

Figure 1:
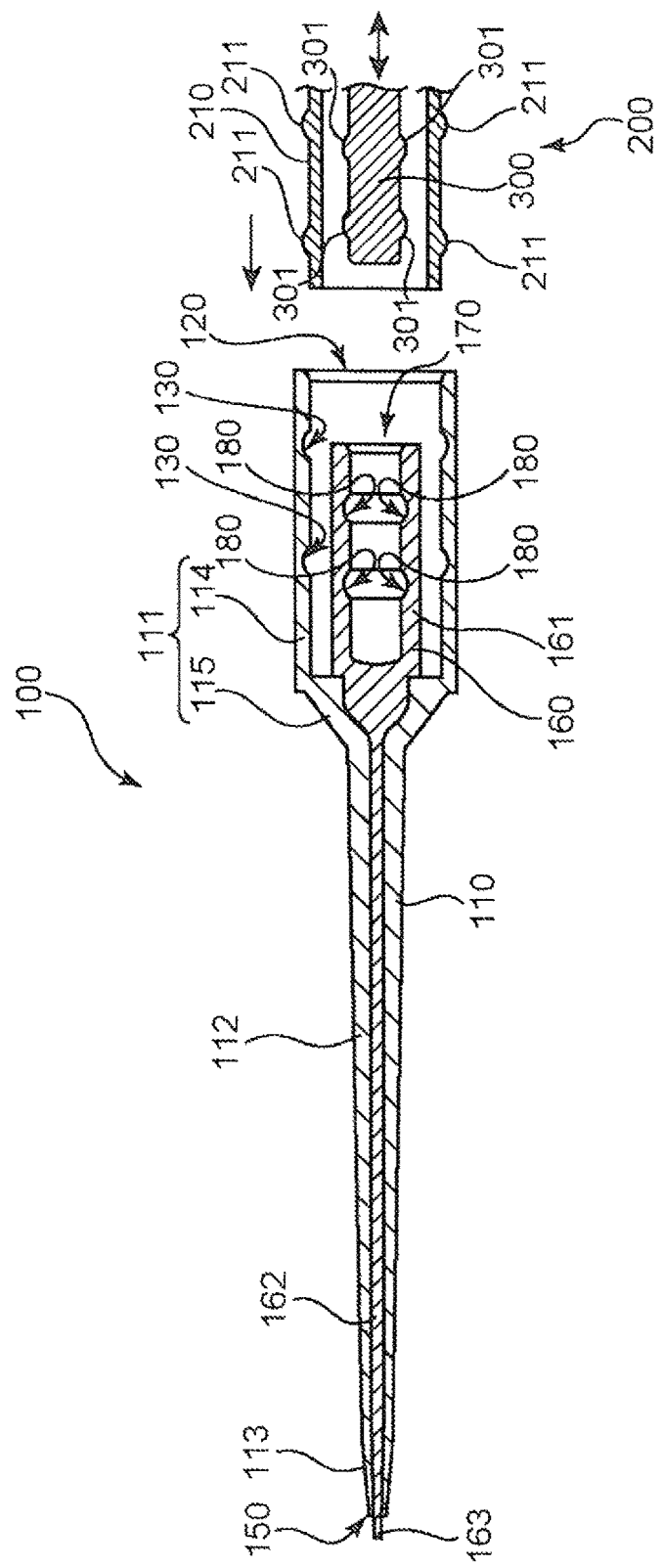
FIG. 1 is a sectional view illustrating a configuration of an aspiration tip according to a first embodiment of the present disclosure.

Hereinafter, an aspiration tip according to a first embodiment of the present disclosure will be described in detail with reference to the accompanying drawings. FIG. 1 is a sectional view illustrating a configuration of an aspiration tip 100 according to the first embodiment. FIG. 2 is a schematic view of an aspiration pipet 200 attached with the aspiration tip 100 according to the first embodiment. The aspiration tip 100 of the first embodiment is used as a jig to aspirate a cell aggregation (spheroid or object) by being attached to a nozzle section 210 of the aspiration pipet 200. The aspiration pipet 200 is a tubular member capable of generating an aspiration force. The aspiration pipet 200 can generate an aspiration force in a tubular passage of the aspiration tip 100 to thereby aspirate a cell aggregation through an aspiration opening 150 formed in a distal end of the tubular passage (at the other end 117t of a second conical part 117, see FIG. 4) of the aspiration tip 100. The aspiration tip 100 includes a syringe section 110 having an inner tubular passage defining an aspiration path for aspirating a cell aggregation, and a plunger 160 movable back and forth in the tubular passage while coming in contact with an inner wall surface of the tubular passage.

(Syringe Section)

FIGS. 3A and 3B are schematic views illustrating a configuration of the syringe section 110 according to the first embodiment, FIG. 3A being a side view of the syringe section 110, and FIG. 3B being a sectional view of the syringe section 110. The syringe section 110 includes a syringe base end portion 111, a syringe main body portion 112, and a syringe leading end portion 113.

The syringe base end portion 111 is formed to be attached to the nozzle section 210 of the aspiration pipet 200, and includes a syringe large diameter part 114, a syringe connecting part 115, and a bulging part 140 (receiving part).

The syringe large diameter part 114 is substantially in the form of a cylinder, and has one end 114s formed with a connection port 120 into which a front end of the nozzle section 210 is inserted, and the other end 114t connecting with one end 115s of the syringe connecting part 115. Two circumferential grooves 130 are formed in an inner wall of the syringe large diameter part 114. Two circumferential ridges 211 formed on an outer peripheral surface of the nozzle section 210 are respectively engaged in these grooves 130, whereby the syringe section 110 is held on the front end of the nozzle section 210. The number of grooves 130 is not particularly limited, but at least one groove 130 is required. The grooves 130 are not limited to a particular shape and may be formed in a spiral shape other than the circumferential shape. Further, the depth of the grooves 130 is not particularly limited as long as the depth is sufficient to allow the ridges 211 of the nozzle section 210 to be attached properly strongly and prevent the aspiration tip 100 attached to the aspiration pipet 200 from being easily detached. The depth is set in the range of about 0.1 to 0.5 mm, for example. In the first embodiment, the grooves 130 have a depth of about 0.2 mm. The grooves 130 may be omitted.

The length of the syringe large diameter part 114 is not particularly limited, and is set to an appropriate value based on the length of the nozzle section 210 to be attached thereto, or the like. The length of the syringe large diameter part 114 is set in the range of about 4 to 16 mm, for example. In the first embodiment, the syringe large diameter part 114 has a length of about 8 mm.

The diameter of a tubular passage portion 114p extending in the syringe large diameter part 114 (the inner diameter of the syringe large diameter part 114) is not particularly limited, and is set to an appropriate value based on the outer diameter of the nozzle section 210 that is inserted into the connection port 120, or the like. The diameter of the tubular passage portion 114p is set in the range of about 1.8 to 10 mm, for example. In the first embodiment, the tubular passage portion 114p has a diameter of about 3.6 mm.

The outer diameter of the syringe large diameter part 114 is not particularly limited, and is set, in the same manner as the inner diameter thereof, based on the outer diameter of the nozzle section 210 to be attached thereto, or the like. The outer diameter of the syringe large diameter part 114 is set in the range of about 2 to 12 mm, for example. In the first embodiment, the syringe large diameter part 114 has an outer diameter of about 4.2 mm.

The syringe connecting part 115 connects the syringe large diameter part 114 and the syringe main body portion 112, and has the one end 115s connecting with the other end 114t of the syringe large diameter part 114 and the other end 115t connecting with one end 112s of the syringe main body portion 112. The syringe connecting part 115 is substantially in the form of a truncated cone having an outer periphery diametrically increasing from the syringe main body portion 112 side to the syringe large diameter part 114 side to connect the syringe main body portion 112 having a smaller outer diameter than the syringe large diameter part 114 to the syringe large diameter part 114.

The length of the syringe connecting part 115 is not particularly limited, and is set in the range of about 0.9 to 5 mm, for example. In the first embodiment, the syringe connecting part 115 has a length of about 1.8 mm.

The rate of diametrical increase of the syringe connecting part 115 is not particularly limited. For example, in the case that the syringe connecting part 115 has a length of 1.8 mm, the syringe connecting part 115 may be made to have an outer periphery diametrically increasing from the range of about 0.7 to 3 mm at the other end 115t to the range of about 2 to 12 mm at the one end 115s. The first embodiment illustrates the syringe connecting part 115 having an outer periphery diametrically increasing from 1.4 mm at the other end 115t to 4.2 mm at the one end 115s.

Further, the diameter of a tubular passage portion 112p extending in the syringe main body portion 112 described later (the inner diameter of the syringe main body portion 112) is smaller than the diameter of the tubular passage portion 114p extending in the syringe large diameter part 114 (the inner diameter of the syringe large diameter part 114). Accordingly, a tubular passage portion 115p of the syringe connecting part 115 diametrically increases from the other end 115t to the one end 115s so as to allow the tubular passage portion 112p and the tubular passage portion 114p having such different diameters to communicate with each other. The rate of diametrical increase is not particularly limited. For example, in the case that the syringe connecting part 115 has a length of 1.8 mm, the tubular passage portion 115p may be made to diametrically increase from the range of about 0.2 to 1.2 mm at the other end 115t to the range of about 0.9 to 11 mm at the one end 115s. The first embodiment illustrates the tubular passage portion 115p diametrically increasing from 0.4 mm at the other end 115t to 1.8 mm at the one end 115s.

The tubular passage portion 115p according to the first embodiment is not limited to a particular shape. In the first embodiment, the inner wall surface (a peripheral surface of the receiving part in the form of a curved recess for receiving a contacting part) of the tubular passage portion 115p is in the form of a curved recess for receiving an outer peripheral surface 165p1 (a peripheral surface of the contacting part in the form of a curved projection) that is in the form of a curved projection and operable to come into contact with the inner wall surface 115p1 of the tubular passage portion 115p when the plunger 160 (see FIGS. 1 and 6A) moves a maximum distance in a discharge direction before and at the time of the aspiration of a cell aggregation. This allows, when the plunger 160 moves the maximum distance in the discharge direction before and at the time of the aspiration of a cell aggregation, the outer peripheral surface 165p1 of a plunger connecting part 165 to come into contact with the inner wall surface 115p1 of the tubular passage portion 115p to thereby stop the plunger 160 from moving in the discharge direction. As a result, a plunger leading end portion 163 described later protrudes from the aspiration opening 150 only by a predetermined length sufficient to permit discharge of air and an object from the syringe section 110, and does not protrude excessively from the aspiration opening 150. This improves the working efficiency and prevents the protruding plunger leading end portion 163 from being damaged.

The bulging part 140 is formed to bulge toward an axial center of the syringe connecting part 115 (a bulging part on the inner wall surface of the syringe connecting part that bulges toward an axial center of the syringe connecting part). The bulging part 140 comes into contact with a plunger step part 166 (see FIG. 6B) of the plunger 160 described later when the plunger 160 moves the maximum distance in the discharge direction before and at the time of the aspiration of a cell aggregation. This allows, when the plunger 160 moves the maximum distance in the discharge direction before and at the time of the aspiration of a cell aggregation, the plunger step part 166 to come into contact with the bulging part 140 to thereby stop the plunger 160 from moving in the discharge direction. As a result, the plunger leading end portion 163 described later protrudes from the aspiration opening 150 only by a predetermined length sufficient to permit discharge of air and an object from the syringe section 110, and does not protrude excessively from the aspiration opening 150. This makes it possible to improve the working efficiency and prevent the protruding plunger leading end portion 163 from being damaged.

The shape and the number of the bulging part 140 is not particularly limited. A single bulging part 140 may be circumferentially formed on the inner wall surface of the syringe connecting part 115, or a plurality of projections may be provided on the inner wall surface of the syringe connecting part 115 at a regular interval as a contacting part. The first embodiment illustrates the single bulging part 140 circumferentially formed on the inner wall surface of the syringe connecting part 115.

The syringe main body portion 112 has the one end 112s connecting with the other end 115t of the syringe connecting part 115, and the other end 112t connecting with one end 116s of a first conical part 116. The syringe main body portion 112 has a linear shape and has an outer periphery having a diameter smaller than that of the syringe connecting part 115 and gradually decreasing from the one end 112s to the other end 112t.

The length of the syringe main body portion 112 (the length of the tubular passage portion 112p) is not particularly limited, and is set to an appropriate value based on a volume to be aspirated, or the like. The length of the syringe main body portion 112 is set in the range of about 3 to 130 mm, for example. In the first embodiment, the syringe main body portion 112 has a length of about 17 mm.

The rate of diametrical reduction of the syringe main body portion 112 is not particularly limited. For example, in the case that the syringe main body portion 112 has a length of 17 mm, the syringe main body portion 112 may be made to have an outer periphery diametrically decreasing from the range of about 0.7 to 3 mm at the one end 112s to the range of about 0.3 to 3 mm at the other end 112t. The first embodiment illustrates the syringe main body portion 112 having an outer periphery diametrically decreasing from 1.4 mm at the one end 112s to 0.6 mm at the other end 112t. The syringe main body portion 112 does not necessarily diametrically decrease and may be made to have a constant outer diameter.

The tubular passage portion 112p is in the form of a cylinder having a constant inner diameter (the tubular passage is disposed in the syringe main body portion and is in the form of a cylinder having a constant inner diameter). Therefore, when the plunger 160 described later (see FIG. 6A) moves in the tubular passage portion 112p, an outer peripheral surface of a plunger main body portion 162 is likely to come into close contact with an inner wall surface of the syringe main body portion 112. Consequently, air is less likely to intervene between them at the time of the aspiration and at the time of the discharge. This allows the aspiration tip 100 (see FIG. 1) to aspirate and discharge a cell aggregation efficiently and accurately. The diameter of the tubular passage portion 112p is not particularly limited, and is set to an appropriate value based on the size of a cell aggregation to be aspirated, a volume to be aspirated, the outer diameter of plunger main body portion 162 described later, or the like. The diameter of the tubular passage portion 112p is set in the range of about 0.2 to 1.2 mm, for example. In the first embodiment, the tubular passage portion 112p has a diameter of 0.4 mm.

Figure 4:
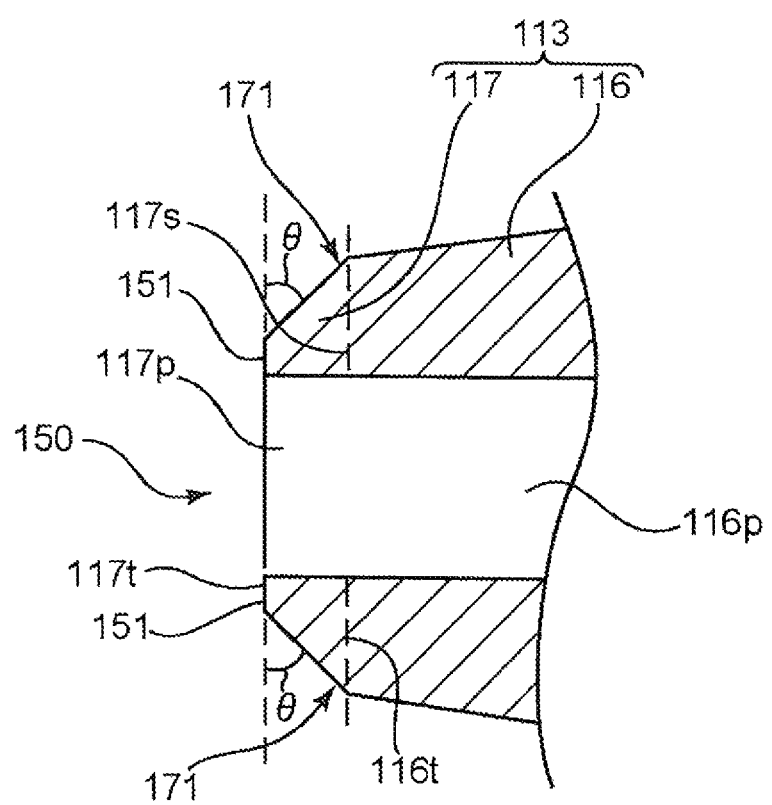
FIG. 4 is an enlarged sectional view of a syringe leading end portion according to the first embodiment of the present disclosure.

FIG. 4 is an enlarged sectional view of the syringe leading end portion 113. The syringe leading end portion 113 includes the first conical part 116 and the second conical part 117 joining the first conical part 116.

The first conical part 116 has the one end 116s (see FIG. 3B) connecting with the syringe main body portion 112 and the other end 116t opposite to the one end 116s. The other end 116t connects with one end 117s of the second conical part 117. The first conical part 116 is substantially in the form of a truncated cone narrowing from the one end 116s to the other end 116t at a first reduction rate.

The length of the first conical part 116 is not particularly limited, and is set in the range of about 1 to 10 mm. In the first embodiment, the first conical part 116 has a length of about 3 mm.

The first reduction rate is not particularly limited. For example, in the case that the first conical part 116 has a length of 3 mm, the first conical part 116 may be made to have an outer periphery decreasing from the range of about 0.3 to 3 mm at the one end 116s to the range of 0.1 to 2.8 mm at the other end 116t. The first reduction rate may be equal to the above-described rate of diametrical reduction of the syringe main body portion 112. In this case, the syringe main body portion 112 and the first conical part 116 are continuously formed. In the first embodiment, the first conical part 116 is made to have an outer diameter of 0.6 mm at the one end 116s and an outer diameter of 0.3 mm at the other end 116t.

The diameter of a tubular passage portion 116p extending in the first conical part 116 is not particularly limited, and is set based on the size of a cell aggregation to be aspirated or the like. The diameter of the tubular passage portion 116p is set in the range of about 0.04 to 1.2 mm, for example. In the first embodiment, the tubular passage portion 116p is made to have a diameter of 0.4 mm at the one end 116s and a diameter of 0.18 mm at the other end 116t.

The second conical part 117 has the one end 117s connecting with the other end 116t of the first conical part 116, and the other end 117t having a leading end surface 151 bearing the aspiration opening 150. The second conical part narrows from the one end 117s to the other end 117t at a second reduction rate.

The length of the second conical part 117 is not particularly limited, and is set in the range of 0.03 to 1 mm, for example. In the first embodiment, the second conical part 117 has a length of about 0.14 mm.

The second reduction rate is greater than the above-described first reduction rate. The second reduction rate is not particularly limited. For example, in the case that the second contracting part 117 has a length of 0.14 mm, the second conical part 117 may be made to have an outer periphery diametrically decreasing from the range of about 0.1 to 2.8 mm at the one end 117s to the range of about 0.05 to 2.5 mm at the other end 117t. In the first embodiment, the second conical part 117 is made to have an outer diameter of 0.3 mm at the one end 117s and an outer diameter of 0.22 mm at the other end 117t.

Figure 5A:
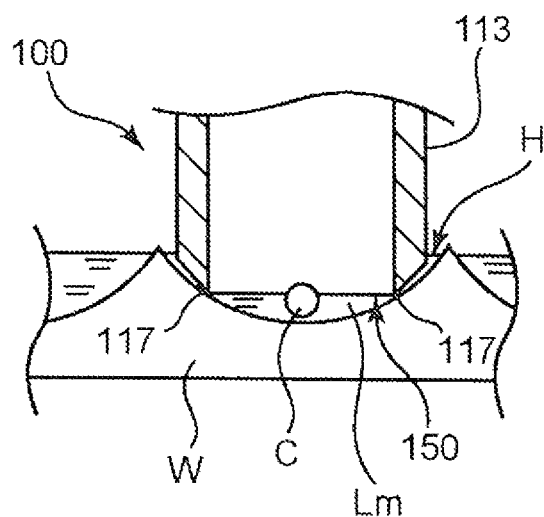
FIGS. 5A and 5B are schematic views illustrating the syringe leading end portion placed in a holding hole of a culture well, FIG. 5A being a schematic view illustrating the syringe leading end portion including a second conical part, and FIG. 5B being a schematic view illustrating a syringe leading end portion including no second conical part.
Figure 5B:
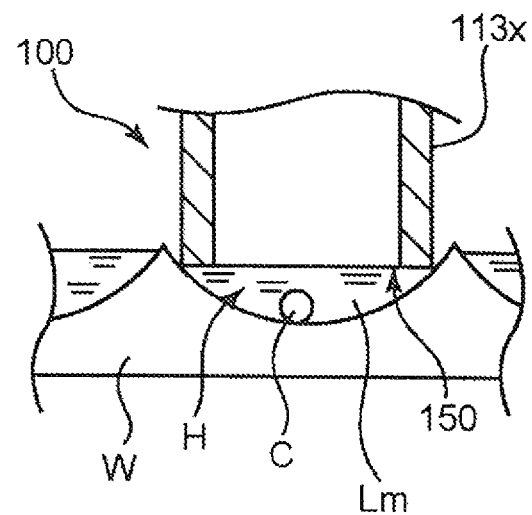

FIGS. 5A and 5B are schematic views illustrating the syringe leading end portion 113 inserted in a holding hole H of a culture well W, FIG. 5A illustrating the inserted syringe leading end portion 113 including the second conical part 117, and FIG. 5B illustrating an inserted syringe leading end portion 113X (another example of the first embodiment) including no second conical part 117. It should be noted that in FIGS. 5A and 5B, the plunger 160 (see FIG. 1) is omitted for descriptive purposes. The culture well W is in the form of a flat and a substantially cuboid container, and includes the holding hole H recessed downward from the top surface. Cell culture solution Lm including a cell aggregation C is stored in the holding hole H. The cell aggregation C is held at the bottom of the holding hole H. Usually, the cell aggregation C held in the holding hole H is aspirated by the aspiration tip 100 that has been inserted from above. The syringe leading end portion 113 (see FIG. 5A) including the second conical part 117 allows the aspiration opening 150 to go deep into the holding hole H to a position close to the cell aggregation C, as compared to the syringe leading end portion 113X (see FIG. 5B) including no second conical part 117. Even the syringe leading end portion 113 including no second conical part 117, such as one shown in FIG. 5B, can be made to allow an aspiration opening to go deep into the holding hole by increasing the size of the holding hole or modifying the holding hole to have a flat bottom, for example. However, the formation of a large holding hole may make a culture well too large in the case that the culture well including a plurality of large holding holes is manufactured. This may result in a deterioration in the working efficiency and a difficulty in saving space. Further, in the case that a holding hole having a flat bottom is made, a cell aggregation is unlikely to be stably held at a predetermined position, so that the cell aggregation may be difficult to be aspirated. However, in the first embodiment, the syringe leading end portion 113 includes the second conical part 117 to allow the aspiration opening 150 to go deep into the holding hole H. Therefore, there is no need to increase the size of the holding hole H or modifying the holding hole H to have a flat bottom. As a result, the cell aggregation C is likely to be stably held and easily aspirated during the aspiration. Further, the culture well W can be made to include a plurality of holding holes H disposed in close proximity to one another. This makes it possible to achieve high working efficiency while saving space even in the case that a plurality of cell aggregations C are aspirated. The outer peripheral surface of the second conical part 117 is not limited to be tapered, and may be curved along the culture well W, for example.

With reference back to FIGS. 3 and 4, the shape of the second conical part 117 can be specified based on the angle θ of a tapered surface 171 with respect to the leading end surface 151 bearing the aspiration opening 150, other than based on the above-described second reduction rate. Specifically, the second conical part 117 can be specified to have the tapered surface 171 tapered at the range of 30 to 80 degrees with respect to the leading end surface 151, for example. The first embodiment illustrates the second conical part 117 having the tapered surface 171 tapered at 60 degrees with respect to the leading end surface.

The diameter of a tubular passage portion 117p extending in the second conical part 117 is not particularly limited, and is set to an appropriate value based on the size of a cell aggregation to be aspirated, or the like. The diameter of the tubular passage portion 117p is set in the range of about 0.04 to 1.2 mm, for example. In the first embodiment, the tubular passage portion 117p has a diameter of 0.18 mm.

The diameter of the aspiration opening 150 is not particularly limited, and is set to an appropriate value based on the size of a cell aggregation to be aspirated. For example, in the case that a cell aggregation has a size of 40 to 200 μm, the diameter of the aspiration opening 150 may be set in the range of 0.04 to 1.2 mm. In the first embodiment, the aspiration opening 150 has a diameter of about 0.18 mm. It should be noted that in the case that a cell aggregation is relatively soft as described later, even if the diameter of the aspiration hole 150 is smaller than the size of the cell aggregation, the cell aggregation may be appropriately deformed to be aspirated at the time of the aspiration.

Therefore, the aspiration opening 150 is not necessarily made to have a diameter greater than the size of a cell aggregation.

Returning to the description of the syringe section 110 as a whole, the material of the syringe section 110 is not limited to a particular kind, and materials that are used for the conventional aspiration tips (such as resin materials and metal materials) can be adopted. For example, a resin such as polypropylene or polystyrene, or glass can be used as the material. Among these materials, use of a resin as the material of the syringe section 110 allows the connection port 120 to appropriately expand when the syringe section 110 is connected to the aspiration pipet 200, so that the syringe section 110 connects with the nozzle section 210 of the aspiration pipet 200 while firmly sticking thereto. Further, among these materials, it is preferred to use a material having a higher rigidity than the material of the plunger 160 (see FIG. 6A) described later. In this case, the syringe section 110 is unlikely to shift due to a stress applied from the plunger 160 when the plunger 160 moves back and forth with an outer peripheral surface thereof coming in contact with the inner wall surface of the syringe section 110. Specifically, when the plunger 160 moves back and forth with the outer peripheral surface thereof coming in contact with the inner wall surface of the syringe section 110, a radial shift of the leading end surface 151 is suppressed to 10 μm or less. Consequently, even in the case that a minute object such as a cell aggregation is aspirated, the aspiration can be performed while maintaining the relative positions of the cell aggregation and the aspiration opening 150. This improves the aspiration accuracy of the aspiration tip 100. The first embodiment illustrates the syringe section 110 made of polypropylene.

Because the syringe section 110 of the first embodiment includes the tubular passage having the above-mentioned diameter and length, it is possible to aspirate cell culture solution (including a cell aggregation) up to about 5 μl, for example. Further, it is also possible to aspirate an extremely small amount, e.g., about 0.01 μl of cell culture solution owing to that the plunger 160 described later moves in the tubular passage of the syringe section 110 while making contact therewith.

The thickness of the tubular wall of the syringe section 110 is not particularly limited. In the first embodiment, the thickness of the tubular wall of the syringe section 110 is set based on the strength, the length of the plunger 160 that moves in the syringe section, or the like, for example, in the range of about 50 to 600 μm.

(Plunger)

Figure 6A:
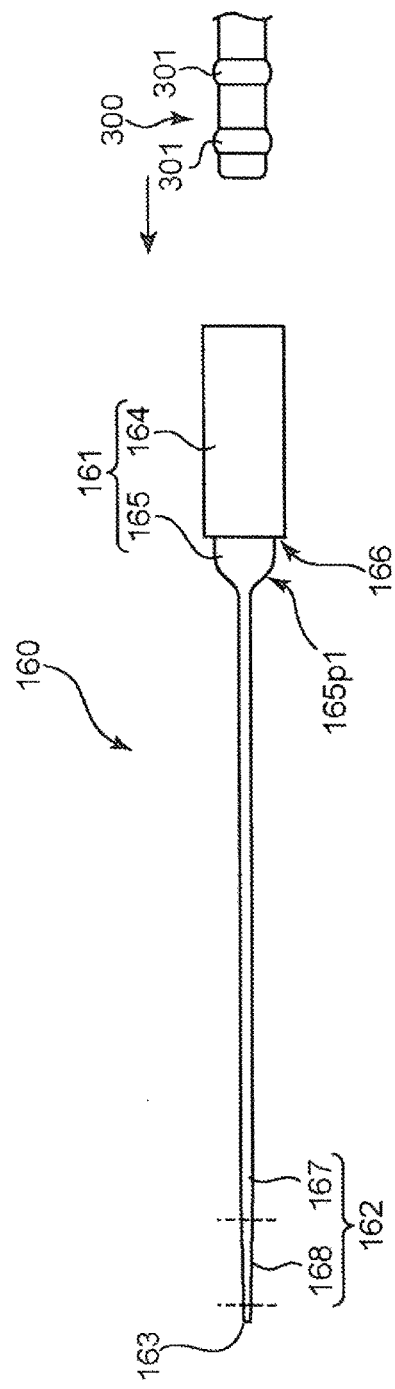
FIGS. 6A and 6B are schematic views illustrating a configuration of a plunger according to the first embodiment of the present disclosure, FIG. 6A being a side view of the plunger, and FIG. 6B being a sectional view of the plunger.
Figure 6B:
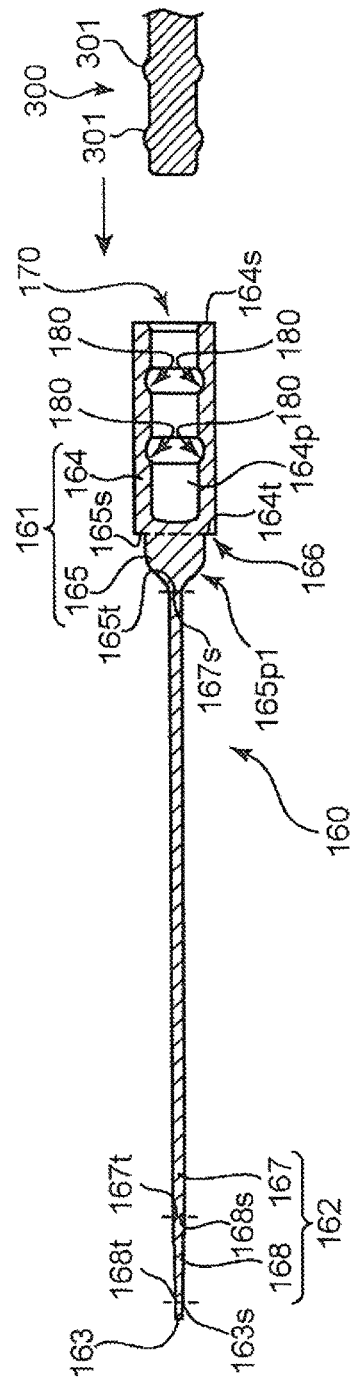

FIGS. 6A and 6B are schematic views illustrating a configuration of the plunger 160 according to the first embodiment, FIG. 6A being a side view of the plunger 160, and FIG. 6B being a sectional view of the plunger 160. The plunger 160 includes a plunger base end portion 161, the plunger main body portion 162, the plunger leading end portion 163, and the plunger step part 166 (contacting part). The plunger main body portion 162 includes a first main body part 167 substantially in the form of a cylinder, and a second main body part 168 joining the first main body part 167.

The plunger base end portion 161 is formed to be attached to a movable member 300 of the aspiration pipet 200 (see FIG. 1), and is placed in the syringe base end portion 111. The plunger base end portion 161 includes a plunger large diameter part 164 and the plunger connecting part 165. The plunger 160 moves back and forth while coming in contact with the inner wall surface of the syringe section 110 (see FIG. 3). Specifically, the plunger 160 moves back and forth with an outer peripheral surface of the first main body part 167 coming in contact with the inner wall surface of the syringe main body portion 112.

The plunger large diameter part 164 is substantially in the form of a cylinder and is placed in the syringe large diameter part 114. The plunger large diameter part 164 has one end 164s formed with a connection port 170 into which a front end of the movable member 300 is inserted, the movable member 300 being movable back and forth at the front end of the nozzle section 210 of the aspiration pipet 200, and the other end 164t connecting with one end 165s of the plunger connecting part 165. Two circumferential grooves 180 are formed in an inner wall of the plunger large diameter part 164. Two circumferential ridges 301 formed on an outer peripheral surface of the movable member 300 are engaged in these grooves 180, whereby the plunger 160 is held on the front end of the movable member 300. The number of grooves 180 is not particularly limited, but at least one groove 180 is required. The grooves 180 are not limited to a particular shape and may be formed in a spiral shape other than the circumferential shape. Further, the depth of the grooves 180 is not particularly limited as long as the depth is sufficient to allow the ridges 301 of the movable member 300 to have a strong attachment and prevent the plunger 160 from being easily detached. The depth is set in the range of about 0.08 to 0.5 mm, for example. In the first embodiment, the grooves 180 have a depth of about 0.15 mm. The grooves 180 may be omitted.

The movable member 300 moves back and forth at the front end of the nozzle section 210 of the aspiration pipet 200 cooperatively with movement of a push button 220 (see FIG. 2) of the aspiration pipet 200. Specifically, a user pushes down the push button 220 to thereby allow the movable member 300 to move in a push-down direction (in the direction of an arrow A1) from the front end of the aspiration pipet 200. On the other hand, a user pulls up the push button 220 to thereby allow the movable member 300 to move in a pull-up direction of the aspiration pipet 200 (in the direction of an arrow A2). With the movement of the movable member 300, the plunger 160 attached to the movable member 300 moves back and forth with the outer peripheral surface of the first main body part 167 coming in contact with the inner wall surface of the syringe main body portion 112.

The length of the plunger large diameter part 164 is not particularly limited, and is set to an appropriate value based on the length of the movable member 300 to be attached thereto, or the like. The length of the plunger large diameter part 164 is set in the range of about 2.8 to 12 mm, for example. In the first embodiment, the plunger large diameter part 164 has a length of about 5.6 mm.

The inner diameter of the plunger large diameter part 164 is not particularly limited, and is set to an appropriate value based on the outer diameter of the movable member 300 that is inserted into the connection port 170, or the like. The diameter of a tubular passage 164p extending in the plunger large diameter part 164 is set in the range of about 0.7 to 4.5 mm, for example. In the first embodiment, the tubular passage 164p has a diameter of about 1.45 mm.

The outer diameter of the plunger large diameter part 164 is not particularly limited, and is set, in the same manner as the inner diameter thereof, based on the outer diameter of the movable member 300 to be attached thereto, or the like. The outer diameter of the plunger large diameter part 164 is set in the range of about 1 to 7 mm, for example. In the first embodiment, the plunger large diameter part 164 has an outer diameter of about 2.2 mm.

The plunger connecting part 165 connects the plunger large diameter part 164 and the plunger main body portion 162. The plunger connecting part 165 has the one end 165s connecting with the other end 164t of the plunger large diameter part 164 and the other end 165t connecting with one end 167s of the first main body part 167. The plunger connecting part 165 is substantially in the form of a hemisphere having an outer periphery diametrically increasing from the other end 165t to the one end 165s to connect the plunger main body portion 162 having a smaller outer diameter than the plunger large diameter part 164 to the plunger large diameter part 164.

The length of the plunger connecting part 165 is not particularly limited, and is set in the range of about 1 to 6 mm, for example. In the first embodiment, the plunger connecting part 165 has a length of about 2.1 mm.

The rate of diametrical increase is not particularly limited. For example, in the case that the plunger connecting part 165 has a length of 2.1 mm, the plunger connecting part 165 may be made to have an outer periphery diametrically increasing from the range of about 0.2 to 0.8 mm at the other end 165t to the range of about 0.8 to 6 mm at the one end 165s. The first embodiment illustrates the substantially hemispherical plunger connecting part 165 having an outer periphery diametrically increasing from 0.39 mm at the other end 165t to 1.7 mm at the one end 165s.

Here, as described above, in the first embodiment, the tubular passage portion 115p (see FIG. 3B) extending in the syringe connecting part 115 is curved to allow the outer peripheral surface 165p1 of the substantially hemispherical plunger connecting part 165 to come into contact therewith. This allows, when the plunger 160 moves the maximum distance in the discharge direction before and at the time of the aspiration of a cell aggregation, the outer peripheral surface 165p1 of the plunger connecting part 165 to come into contact with the inner wall surface 115p1 of the tubular passage portion 115p to thereby restrict the plunger 160 from moving in the discharge direction.

Further, as described above, in the first embodiment, the plunger large diameter part 164 has an outer diameter of 2.2 mm, and the plunger connecting part 165 has an outer diameter of 1.7 mm at the one end 165s. Consequently, the plunger step part 166 (contacting part disposed on an outer peripheral surface of the plunger base end portion) is defined by the connecting portion of the plunger connecting part 165 and the plunger large diameter part 164. Further, as described above, the bulging part 140 (see FIG. 3B) is formed on the inner wall surface of the syringe connecting part 115 of the syringe section 110. This allows, when the plunger 160 moves the maximum distance in the discharge direction before and at the time of the aspiration of a cell aggregation, the plunger step part 166 to come into contact with the bulging part 140 to thereby restrict the plunger 160 from moving in the discharge direction.

The plunger main body portion 162 has a smaller diameter than the plunger base end portion 161, and is substantially in the form of a stick. The plunger main body portion 162 includes the first main body part 167 substantially in the form of a cylinder, and the second main body part 168 joining the first main body part 167. The plunger main body portion 162 moves back and forth in the syringe section 110 with the outer peripheral surface of the first main body part 167 mainly coming in contact with the inner wall surface of the syringe main body portion 112.

The first main body part 167 has one end 167s connecting with the plunger connecting part 165, and the other end 167t connecting with one end 168s of the second main body part 168. The first main body part 167 is in the form of a cylinder having a constant outer diameter. Therefore, when the plunger 160 moves back and forth in the tubular passage, the cylindrical outer peripheral surface of the first main body part 167 is likely to come into close contact with the above-mentioned inner wall surface of the syringe main body portion 112 (the inner wall surface of the tubular passage portion 112p, see FIG. 3B). Consequently, air is less likely to intervene between them at the time of the aspiration and at the time of the discharge. This allows the aspiration tip 100 (see FIG. 1) to aspirate and discharge an object efficiently and accurately.

The length of the first main body part 167 is not particularly limited, and is set to an appropriate value based on the length of the syringe main body portion 112 or the like. The length of the first main body part 167 is set in the range of about 3 to 130 mm, for example. In the first embodiment, the first main body part 167 has a length of about 17 mm.

The outer diameter of the first main body part 167 is not particularly limited, and is set to an appropriate value based on the inner diameter of the syringe main body portion 112 or the like. The outer diameter of the first main body part 167 is set in the range of about 0.2 to 0.8 mm, for example. In the first embodiment, the first main body part 167 has an outer diameter of about 0.39 mm. The outer diameter of the first main body part 167 is not necessarily exactly equal to the inner diameter of the syringe main body portion 112. In other words, the outer diameter of the first main body part 167 only needs to be sufficient to allow the first main body part 167 to come into contact with the inner wall surface of the syringe section 110 to discharge substantially the whole amount of air from the syringe section 110 before the aspiration, and discharge the whole cell aggregation without leaving any particles on the inner wall surface of the syringe section 110 at the time of the discharge, as described later. Therefore, the outer diameter of the first main body part 167 may be set to be slightly smaller than the inner diameter of the syringe main body portion 112.

The second main body part 168 has the one end 168s connecting with the other end 167t of the first main body part 167, and the other end 168t connecting with one end 163s of the plunger leading end portion 163. As described later, the outer diameter of the plunger leading end portion 163 is set to be substantially equal to the diameter of the aspiration opening 150. In the first embodiment, the aspiration opening 150 has a diameter of about 0.18 mm as mentioned above. Therefore, the second main body part 168 is provided to connect the two portions (the plunger leading end portion 163 and the first main body part 167) having different diameters.

The length of the second main body part 168 is not particularly limited, and is set to an appropriate value based on the length of the syringe leading end portion 113 or the like. The length of the second main body part 168 is set in the range of about 1.2 to 12 mm, for example. In the first embodiment, the second main body part 168 has a length of about 3.7 mm.

The outer diameter of the second main body part 168 is not particularly limited, and is set to an appropriate value based on the inner diameter of the syringe leading end portion 113, the outer diameter of the plunger leading end portion 163 described later, or the like. The outer diameter of the second main body part 168 is set in the range of about 0.03 to 2.1 mm, for example. In the first embodiment, the second main body part 168 has an outer diameter of about 0.17 mm to 0.39 mm. The outer periphery of the second main body part 168 may be made to diametrically decrease from the one end 168s to the other end 168t either at a predetermined reduction rate or stepwise so as to have a diameter of about 0.17 mm at the other end 168t. The first embodiment illustrates the second main body part 168 having an outer periphery diametrically decreasing from the one end 168s toward the other end 168t to have an outer diameter of about 0.17 mm at the specific position that is 2.5 mm away from the one end 168s, and diametrically uniform from the specific position to the other end 168t.

The plunger leading end portion 163 is substantially in the form of a cylinder having the one end 163s connecting with the other end 168t of the second main body part 168. The plunger leading end portion 163 protrudes from the aspiration opening 150 before the aspiration of a cell aggregation and at the time of the discharge of the cell aggregation and retracts in the syringe section 110 at the time of the aspiration of the cell aggregation.

The length of the plunger leading end portion 163 is not particularly limited, and only needs to be sufficient to allow the discharge of air and a cell aggregation from the syringe section 110 before the aspiration of the cell aggregation and at the time of the discharge of the cell aggregation. The length of the plunger leading end portion 163 is set to 0.6 to 3.6 mm, for example. By setting the length of the plunger leading end portion 163 within such a range, it is possible to discharge air and a cell aggregation from the syringe section 110 while preventing the plunger leading end portion 163 from excessively protruding from the aspiration opening 150 and getting damaged. The first embodiment illustrates the plunger leading end portion 163 protruding from the aspiration opening 150 by 0.6 mm.

The outer diameter of the plunger leading end portion 163 is not particularly limited, and is set to an appropriate value that is approximately equal to the diameter of the aspiration opening 150 based on the diameter of the aspiration opening 150 (see FIG. 3A and FIG. 4). As described above, the diameter of the aspiration opening 150 may be set in the range of 0.04 to 2.2 mm and, in the first embodiment, the aspiration opening 150 has a diameter of about 0.18 mm. Accordingly, the outer diameter of the plunger leading end portion 163 is set in the range of about 0.03 to 2.1 mm, for example. In the first embodiment, the plunger leading end portion 163 has an outer diameter of 0.17 mm. Thus, in the first embodiment, the outer diameter of the plunger leading end portion 163 is set to be approximately equal to the diameter of the aspiration opening 150. Therefore, when the plunger leading end portion 163 protrudes from the aspiration opening 150 before the aspiration of a cell aggregation and at the time of the discharge of the cell aggregation, air and the cell aggregation are unlikely to remain in the syringe section 110 and thus substantially all the amount thereof can be discharged. Further, these air and cell aggregations are unlikely to adhere to the periphery of the aspiration opening 150. Consequently, even in the case that the aspiration tip 100 (see FIG. 1) is used repeatedly, sample contamination is unlikely to occur between the samples that have been successively taken.

Returning to the description of the plunger 160 as a whole, the material of the plunger 160 is not limited to a particular kind and, for example, a resin such as polyacetal, polyethylene, and polystyrene can be used. Among these materials, it is preferred to use a material having a lower rigidity than the material of the syringe section 110. The first embodiment illustrates the plunger 160 made of polyacetal.

(Operation of Aspiration and Discharge)

Now, aspiration and discharge of a cell aggregation using the aspiration tip 100 according to the first embodiment will be described. The first embodiment illustrates an operation of aspirating a cell aggregation C contained in cell culture solution Lm1 stored in a container C1 that opens at the top, such as a petri dish, and then discharging the cell aggregation. FIGS. 7A to 7D are schematic views illustrating an operation of aspirating and discharging a cell aggregation C using the aspiration tip 100 according to the first embodiment, FIG. 7A illustrating a state that the plunger leading end portion 163 is retracted in the syringe section 110 before the aspiration, FIG. 7B illustrating a state that the plunger leading end portion 163 protrudes from the aspiration opening 150 before the aspiration, FIG. 7C illustrating a state that the aspiration opening 150 has approached the cell aggregation C, FIG. 7D illustrating a state that the cell aggregation C (cell aggregation Ca) is being aspirated, and FIG. 7E illustrating a state that the cell aggregation C (cell aggregation Cb) is being discharged.

Before the aspiration, the aspiration tip 100 is in the state that the plunger leading end portion 163 is retracted in the syringe section 110 (see FIG. 7A) or that the plunger leading end portion 163 protrudes from the aspiration opening 150 (see FIG. 7B). In the first embodiment, in the case that the plunger leading end portion 163 is retracted in the syringe section 110 of the aspiration tip 100 as shown in FIG. 7A, the plunger 160 is moved in a discharge direction (in the direction of an arrow A3) to cause the plunger leading end portion 163 to protrude from the aspiration opening 150 to thereby shift to the position shown in FIG. 7B. This allows air existing in the internal space of the syringe main body portion 112 to be discharged. The shift from the position shown in FIG. 7A to the position shown in FIG. 7B is preferred to be performed in the air, but may be performed with the aspiration opening 150 being immersed in the cell culture solution Lm1.

Thereafter, as shown in FIG. 7C, the aspiration opening 150 is brought close to the cell aggregation C. In the case that impurities other than the cell aggregation C are included in the cell culture solution Lm1, the aspiration opening 150 is preferred to be brought as close to the cell aggregation C as possible. At this time, the plunger leading end portion 163 may be moved some distance in an aspiration direction (in the direction of an arrow A4, see FIG. 7D) so that the aspiration opening 150 comes closer to the cell aggregation C.

Thereafter, as shown in FIG. 7D, the plunger 160 is moved in the aspiration direction (in the arrow A4 direction) with the aspiration opening 150 being immersed in the cell culture solution Lm1 to generate an aspiration force in the syringe main body portion 112, so that the cell aggregation is aspirated into the tubular passage portion 112p. The cell aggregation that has been aspirated in the tubular passage portion 112p is shown as a cell aggregation Ca. At this time, because the aspiration opening 150 is immersed in the cell culture solution Lm1, no air flows into the syringe main body portion 112. Further, because no air intervenes in the aspiration, an area Ar that is defined in the syringe main body portion 112 as a result of the movement of the plunger 160 in the aspiration direction is filled with the cell aggregation Ca and the cell culture solution Lm1. This prevents delay in the aspiration (deterioration of response at the time of the aspiration) due to expansion of air, as compared with, for example, the conventional case in which air intervenes in the aspiration. Therefore, it is possible to aspirate an accurate amount of cell aggregation efficiently.

Finally, as shown in FIG. 7E, the plunger 160 is moved in the discharge direction (in the arrow A3 direction) to cause the plunger leading end portion 163 to protrude from the aspiration opening 150, so that the cell aggregation that has been held in the syringe main body portion 112 is discharged to a container C2 storing cell holding solution liquid Lm2 that has been prepared separately. The discharged cell aggregation is shown as a cell aggregation Cb. At this time, the plunger main body portion 162 moves with the outer peripheral surface thereof coming in contact with the inner wall surface of the syringe main body portion 112. This allows the cell aggregation that has been held in the syringe main body portion 112 and the cell culture solution that has been held in the syringe main body part 112 after being aspirated with the cell aggregation to be completely discharged from the syringe main body portion 112. Further, because no air intervenes in the discharge in the same manner as in the aspiration, the movement of the plunger 160 in the discharge direction allows the plunger leading end portion 163 to push out the cell aggregation and the cell culture solution that have been held in the syringe main body portion 112 to thereby discharge them. This prevents delay in the discharge (deterioration of response at the time of the discharge) due to compression of air, as compared with, for example, the conventional case in which air intervenes in the discharge. Therefore, it is possible to discharge an accurate amount of cell aggregation efficiently.

Thus, because no air intervenes when a cell aggregation is aspirated and discharged using the aspiration tip 100 according to the first embodiment, the aspiration speed and the discharge speed are unlikely to decrease, which results in achievement of high working efficiency. Further, because no air intervenes both in the aspiration and in the discharge, the amount of the object that is aspirated is equal to the volume of the area of the syringe section 110 that is defined as a result of retraction of the plunger 160. The cell aggregation that has been aspirated into this area is then completely discharged. Therefore, the aspiration tip 100 of the first embodiment is likely to allow aspiration and discharge of an accurate amount of an object. Further, at the time of the discharge, the plunger main body part 162 moves while coming in contact with the inner wall surface of the syringe main body part 112 to cause the plunger leading end portion 163 to protrude from the aspiration opening 150. Therefore, the cell aggregation and the cell culture solution aspirated with the cell aggregation are likely to be completely discharged without remaining on the inner wall surface or around the aspiration opening 150. Further, because the aspirated object is completely discharged, even in the case that the aspiration tip 100 is used repeatedly, sample contamination is unlikely to occur between the samples that have been successively taken. Further, when a cell aggregation is observed with an observation device such as a microscope while the object is held in the aspiration tip 100, for example, no air exists in the tubular passage, which provides an improved observation accuracy.

(Second Embodiment)
<Aspiration Tip>

Figure 8:
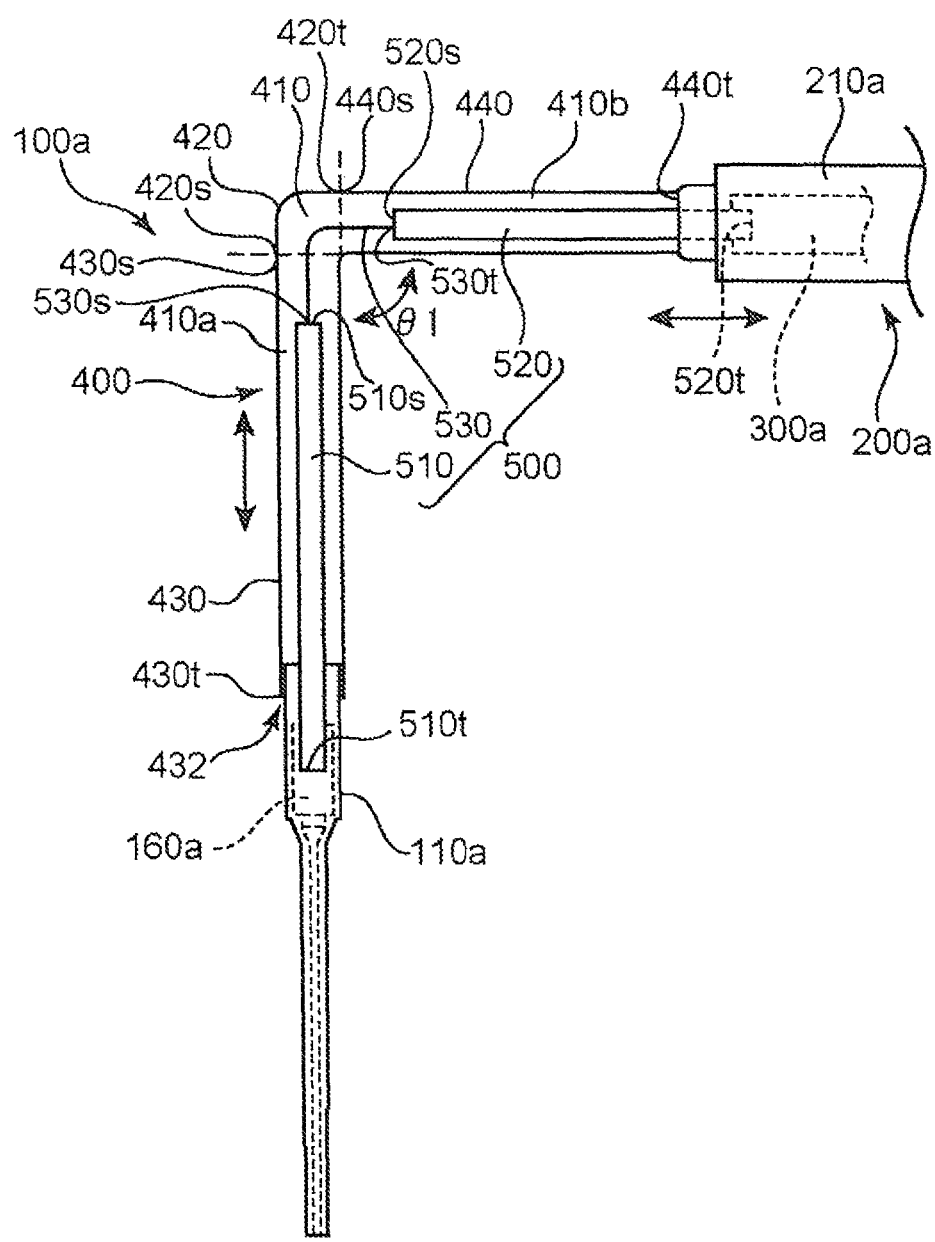
FIG. 8 is a schematic view illustrating a configuration of an aspiration tip according to a second embodiment of the present disclosure.

Hereinafter, an aspiration tip 100a according to a second embodiment of the present disclosure will be described in detail with reference to the accompanying drawings. FIG. 8 is a schematic view illustrating a configuration of the aspiration tip 100a according to the second embodiment. The aspiration tip 100a of the second embodiment includes a syringe section 110a having a tubular passage defining an aspiration path for aspirating a cell aggregation, a plunger 160a movable back and forth while coming in contact with an inner wall surface of the syringe section 110a, a holder section 400 attached to the syringe section 110a and including an internal passage 410 communicating with the tubular passage of the syringe section 110a, and a piston member 500 attached to the plunger 160a and movable back and forth in the holder section 400. In the state of use of the aspiration tip 100a of the second embodiment, the syringe section 110a is substantially oriented in a vertical direction, and a holder rear end portion 440 described later is disposed in a horizontal orientation of extending in a horizontal direction.

(Syringe Section)

Figure 9A:
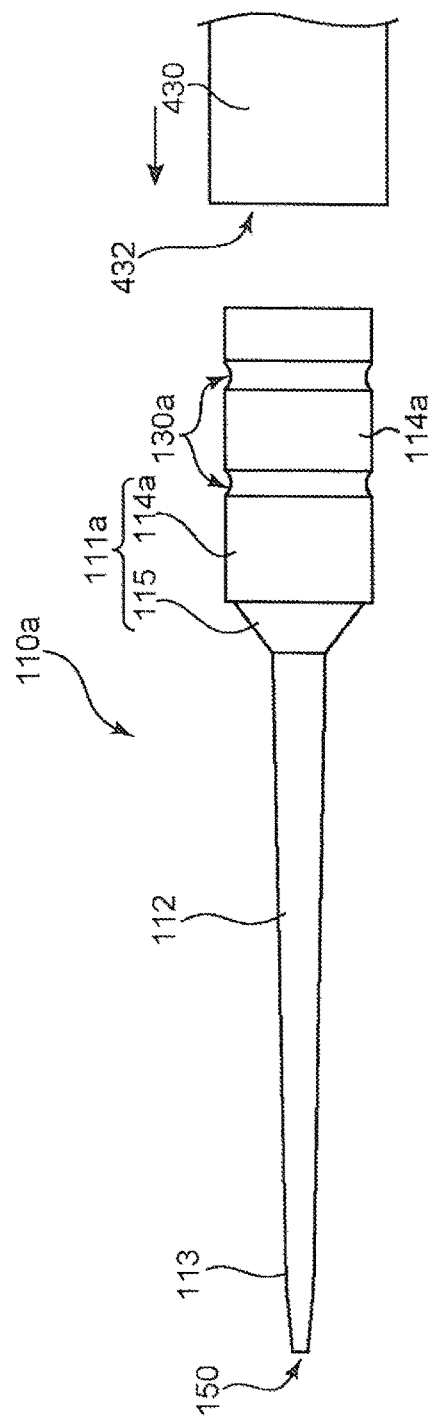
FIGS. 9A and 9B are schematic views illustrating a configuration of a syringe section of the aspiration tip according to the second embodiment of the present disclosure, FIG. 9A being a side view of the syringe section, and FIG. 9B being a sectional view of the syringe section.
Figure 9B:
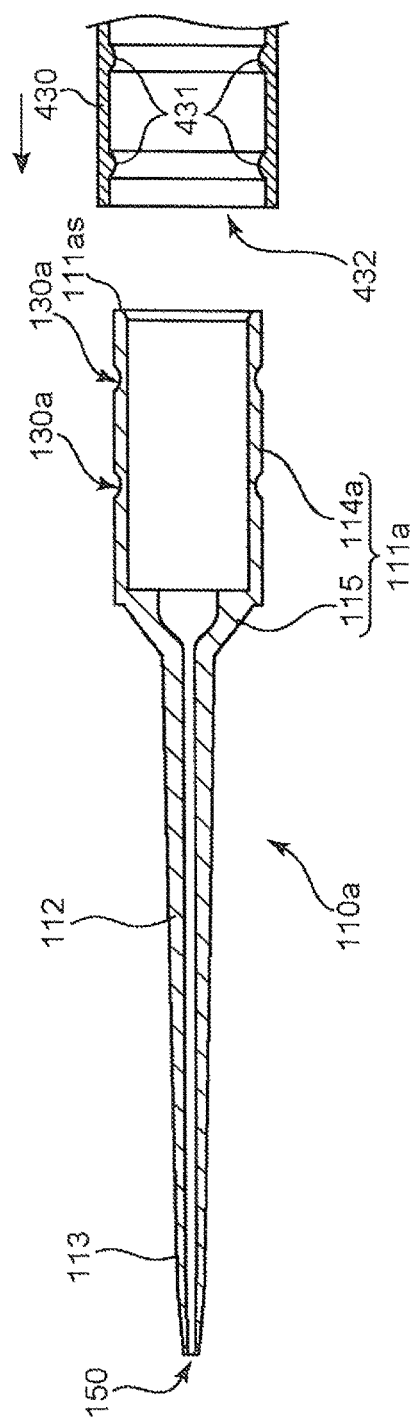

FIGS. 9A and 9B are schematic views illustrating a configuration of the syringe section 110a according to the second embodiment, FIG. 9A being a side view of the syringe section 110a, and FIG. 9B being a sectional view of the syringe section 110a. The syringe section 110a includes a syringe base end portion 111a, a syringe main body portion 112, and a syringe leading end portion 113. The syringe base end portion 111a includes a syringe large diameter part 114a and a syringe connecting part 115a. The syringe section 110a of the second embodiment has a similar configuration to that of the above-described syringe section 110 of the first embodiment except that the syringe section 110a has the other end (see one end 111as of the syringe base end portion 111a described later) that is opposite to the distal end (the other end 117t of a second conical part 117, see FIG. 4) formed with an aspiration opening 150, the other end allowing the holder section 400 to be held thereon. Therefore, elements that have structures identical to those of the syringe section 110 of the first embodiment are denoted by the same reference numerals as in the first embodiment and description thereof will be appropriately omitted.

The syringe base end portion 111a has the one end 111as that is inserted in a holder front end portion 430 described later, and includes the syringe large diameter part 114a substantially in the form of a cylinder, and the syringe connecting part 115.

Two circumferential grooves 130a are formed in an outer wall of the syringe large diameter part 114a. Two circumferential ridges 431 formed on an inner wall surface of the holder front end portion 430 are respectively engaged in these grooves 130a, whereby the syringe section 110a is held on the holder section 400. The number, shape, and size of the grooves 130a are similar to those of the above-described grooves 130 formed in the syringe large diameter part 114 of the first embodiment and, therefore, description thereof will be omitted.

Further, the other structural features of the syringe section 110a are similar to those of the above-described syringe section 110 of the first embodiment and, therefore, description thereof will be omitted.

(Plunger)

FIGS. 10A and 10B are schematic views illustrating a configuration of the plunger 160a according to the second embodiment, FIG. 10A being a side view of the plunger 160a, and FIG. 10B being a sectional view of the plunger 160a. The plunger 160a includes a plunger base end portion 161a, a plunger main body portion 162, and a plunger leading end portion 163. The plunger base end portion 161a includes a plunger large diameter part 164a and a plunger connecting part 165. The plunger 160a of the second embodiment has a similar configuration to that of the above-described plunger 160 of the first embodiment except that the plunger 160a has the other end (see one end 161as of the plunger base end portion described later) that is opposite to the plunger leading end portion 163, the other end allowing a first piston piece 510 described later to be held thereon. Therefore, elements that have structures identical to those of the plunger 160 of the first embodiment are denoted by the same reference numerals as in the first embodiment and description thereof will be appropriately omitted.

The plunger base end portion 161a has the one end 161as formed with a connection port 170a into which a front end of the first piston piece 510 described later is inserted. The plunger base end portion 161a includes the plunger large diameter part 164a substantially in the form of a cylinder, and the plunger connecting part 165.

Two circumferential grooves 180a are formed in an inner wall of the plunger large diameter part 164a. Two circumferential ridges 511 formed on an outer peripheral surface of the first piston piece 510 are respectively engaged in these grooves 180a, whereby the plunger 160a is held on the piston member 500. The number, shape, and size of the grooves 180a are similar to those of the above-described grooves 180 formed in the plunger large diameter part 164 of the first embodiment and, therefore, description thereof will be omitted.

Further, the other structural features of the plunger 160a are similar to those of the above-described plunger 160 of the first embodiment and, therefore, description thereof will be omitted.

(Holder Section)

With reference back to FIG. 8, the holder section 400 is attached to the syringe section 110a, and includes the internal passage 410 communicating with the tubular passage of the syringe section 110a. Further, the holder section 400 includes a bent portion 420 having a substantially L-shape, the holder front end portion 430 disposed in front of the bent portion 420 and attached to the above-mentioned other end of the syringe section 110a (the one end 111as of the syringe base end portion 111a) at the front thereof, and the holder rear end portion 440 disposed behind the bent portion 420 and has the horizontal orientation of extending in the horizontal direction in the state of use. The piston member 500 is disposed in the internal passage 410, the piston member 500 being movable back and forth in the holder section 400.

The bent portion 420 is substantially in the form of an L-shaped tube having one end 420s connecting with one end 430s of the holder front end portion 430, and the other end 420t connecting with one end 440s of the holder rear end portion 440, the bent portion 420 including an internal passage in which a connecting member 530 described later is disposed. The bent portion 420 determines the disposition of the holder rear end portion 440 with respect to the holder front end portion 430 so that the holder rear end portion 440 has the horizontal orientation of extending in the horizontal direction when the holder front end portion 430 is substantially oriented in the vertical direction.

The angle θ1 between the holder front end portion 430 and the holder rear end portion 440 at the bent portion 420 is not particularly limited and may be set at 90 degrees or greater but less than 180 degrees, for example. The second embodiment illustrates the case where the θ1 is set at 90 degrees.

The holder front end portion 430 is substantially in the form of a cylinder, and is substantially oriented in the vertical direction in the state of use, similarly to the syringe section 110a. The holder front end portion 430 has the one end 430s connecting with the bent portion 420 and the other end 430t formed with a connection port 432 in which the syringe large diameter part 114a is inserted. The first piston piece 510 described later protrudes from and retracts into the connection port 432. The two circumferential ridges 431 (see FIG. 9A) are formed on the inner wall surface of the holder front end portion 430, the ridges 431 being engaged in the above-described two grooves 130a formed in the outer wall of the syringe large diameter part 114a.

The outer diameter of the holder front end portion 430 is not particularly limited, and is set to an appropriate value according to the outer diameter of the syringe large diameter part 114a. The outer diameter of the holder front end portion 430 is set in the range of about 3.1 to 18 mm, for example. In the second embodiment, the holder front end portion 430 has an outer diameter of 6.3 mm.

The inner diameter of the holder front end portion 430 is not particularly limited, and is set to an appropriate value based on the outer diameter of the first piston piece 510 described later or the like. The inner diameter of the holder front end portion 430 is set in the range of about 2.1 to 12.1 mm, for example. In the second embodiment, the holder front end portion 430 has an inner diameter of 4.3 mm.

The length of the holder front end portion 430 is not particularly limited, and only needs to be sufficient to allow at least a part of the first piston piece 510 described later to fit in an internal passage 410a of the holder front end portion 430. The length of the holder front end portion 430 is set in the range of about 3 to 12 mm, for example. In the second embodiment, the holder front end portion 430 has a length of 6 mm.

The holder rear end portion 440 is substantially in the form of a cylinder, and is disposed in the horizontal orientation of extending in the horizontal direction in the state of use. The holder rear end portion 440 has the one end 440s connecting with the other end 420t of the bent portion 420, and the other end 440t to be inserted into a nozzle section 210a. Two circumferential grooves (not shown) are formed in a portion of an outer wall of the holder rear end portion 440 that is near the other end 440t. Two circumferential ridges formed on an inner wall surface of the nozzle section 210a are respectively engaged in these grooves. This allows the holder section 400 to be attached to a front end of the nozzle section 210a.

The outer diameter of the holder rear end portion 440 is not particularly limited. The outer diameter of the holder rear end portion 440 is set in the range of about 3.1 to 18 mm, for example. In the second embodiment, the holder rear end portion 440 has an outer diameter of 6.3 mm.

The inner diameter of the holder rear end portion 440 is not particularly limited, and is set to an appropriate value based on an outer diameter of a second piston piece 520 described later or the like. The inner diameter of the holder rear end portion 440 may be set in the range of about 2.1 to 12.1 mm, for example. In the second embodiment, the holder rear end portion 440 has an inner diameter of 4.3 mm.

The length of the holder rear end portion 440 is not particularly limited, and only needs to be sufficient to allow at least a part of the second piston piece 520 described later to fit in an inner passage 410b of the holder rear end portion 440. The length of the holder rear end portion 440 is set in the range of about 15 to 90 mm, for example. In the second embodiment, the holder rear end portion 440 has a length of 30 mm.

Returning to the description of the holder section 400 as a whole, the material of the holder section 400 is not limited to a particular kind, and a resin such as polypropylene or polystyrene, metal, or glass can be used, for example. Among these materials, it is preferred to use a material having a higher rigidity than the material of the piston member 500 described later. In the second embodiment, the holder section 400 is made of stainless steel.

The thickness of the tubular wall of the holder section 400 is not particularly limited. In the second embodiment, the thickness of the tubular wall of the holder section 400 is set based on the strength, the length of the piston member 500 that moves in the holder section 400 or the like, which is, for example, in the range of about 50 to 1,000 μm.

(Piston Member)

The piston member 500 is a member that is inserted in the connection port 170a of the plunger large diameter part 164a, thereby being held on the plunger 160a. The piston member 500 moves back and forth in the holder section 400. More specifically, the piston member 500 includes the first piston piece 510 disposed in the internal passage 410a of the holder front end portion 430, the second piston piece 520 disposed in the internal passage 410b of the holder rear end portion 440, and the connecting member 530 connecting the first piston piece 510 and the second piston piece 520.

The first piston piece 510 is substantially in the form of a cylinder, and has one end 510s connecting with the connecting member 530 and the other end 510t inserted in the connection port 170a of the plunger large diameter part 164a. The first piston piece 510 moves back and forth in the internal passage 410a. This causes the plunger 160a to move back and forth in the syringe section 110a with the first piston piece 510 inserted therein.

The outer diameter of the first piston piece 510 is not particularly limited, and only needs to be smaller than the inner diameter of the holder front end portion 430. The outer diameter of the first piston piece 510 is set in the range of about 0.65 to 4.45 mm, for example. In the second embodiment, the first piston piece 510 has an outer diameter of 1.4 mm.

The length of the first piston piece 510 is not particularly limited, and only needs to be shorter than the holder front end portion 430 so that plunger 160a connecting with the first piston piece 510 can move a sufficient distance to aspirate and discharge a cell aggregation. The length of the first piston piece 510 is set in the range of about 2.5 to 10 mm. In the second embodiment, the first piston piece 510 has a length of 5 mm.

The material of the first piston piece 510 is not limited to a particular kind, and a resin such as polypropylene or polystyrene, glass, or metal can be used, for example. Among these materials, use of a resin allows the first piston piece 510 to appropriately deform when being connected to the plunger large diameter part 164a to be thereby firmly held on the plunger 160a.

The second piston piece 520 is substantially in the form of a cylinder, and has one end 520s connecting with the connecting member 530 and the other end 520t to be connected with a movable member 300a of an aspiration pipet 200a. Specifically, two circumferential ridges (not shown) are formed on a portion of an outer peripheral surface of the second piston piece 520 that is near the other end 520t, and two grooves are formed in an inner wall of a recessed portion (not shown) formed in a front end of the movable member 300a. The ridges are engaged in the grooves of the movable member 300a to thereby connect the second piston piece 520 with the movable member 300a. The movable member 300a moves at the front end of the nozzle section 210a cooperatively with movement of a push button (not shown) of the aspiration pipet 200a. With the movement of the movable member 300a, the second piston piece 520 moves back and forth in the internal passage 410b of the holder rear end portion 440. The second piston piece 520 connects with the first piston piece 510 via the connecting member 530 described later, the first piston piece 510 connecting with the plunger 160a as described above. Consequently, the plunger 160a moves back and forth in the syringe section 110a with the movement of the movable member 300a. The movement of the movable member 300a may be performed by a user or controlled by an actuator (not shown) provided outside.

The outer diameter of the second piston piece 520 is not particularly limited, and only needs to be smaller than the inner diameter of the holder rear end portion 440. The outer diameter of the second piston piece 520 is set in the range of about 2.5 to 10 mm, for example. In the second embodiment, the second piston piece 520 has an outer diameter of 5 mm.

The length of the second piston piece 520 is not particularly limited, and only needs to be shorter than the holder rear end portion 440 so that the first piston piece 510 connecting with the second piston piece 520 via the connecting member 530 and the plunger 160a connecting with the first piston piece 510 can move a sufficient distance to aspirate and discharge a cell aggregation. The length of the second piston piece 520 is set in the range of about 14 to 78 mm. In the second embodiment, the second piston piece 520 has a length of 28 mm.

The material of the second piston piece 520 is not limited to a particular kind, and a resin such as polypropylene or polystyrene, glass, or metal can be used, for example. Among these materials, use of a resin allows the second piston piece 520 to appropriately deform when being connected to the movable member 300a to be thereby firmly held on the movable member 300a.

The connecting member 530 is in the form of a wire having a high rigidity, and has one end 530s connecting with the first piston piece 510 and the other end 530t connecting with the second piston piece 520. The first piston piece 510 and the second piston piece 520 connected by the connecting member 530 are kept at a specific distance from each other. In other words, the connecting member 530 has a function of converting a movement of the second piston piece 520 into a movement of the first piston piece 510. Specifically, when the second piston piece 520 moves in the internal passage 410b of the holder rear end portion 440 owing to movement of the movable member 300a of the aspiration pipet 200a, the first piston piece 510 connected with the second piston piece 520 by the connecting member 530 moves in the internal passage 410a of the holder front end portion 430, with the movement of the second piston piece 520, the same distance as the second piston piece 520. Consequently, the plunger 160a connecting with the first piston piece 510 also moves the same distance in the syringe section 110a. Thus, the movement of the movable member 300a in the nozzle section 210a is transmitted to the plunger 160a in the same manner as in the first embodiment as described above.

The material of the connecting member 530 is not limited to a particular kind, and only needs to have a rigidity sufficient to accurately transmit a movement of the second piston piece 520 to the first piston piece 510. Examples of the material include an iron wire, piano wire, a spring wire, a stainless steel wire, and a resin wire. In the second embodiment, the connecting member 530 is made of a piano wire. The connecting member 530 may be made in the form of a spring other than a wire.

The outer diameter (thickness) of the connecting member 530 is not particularly limited, and only needs to be sufficient to exhibit a rigidity that allows accurate transmission of a movement of the second piston piece 520 to the first piston piece 510. Such thickness ranges from 0.2 to 3 mm, for example, though depending on the material. In the second embodiment, the connecting member 530 has a thickness of 0.5 mm.

As described, the aspiration tip 100a according to the second embodiment allows the syringe section 110a and the plunger 160a to connect with the aspiration pipet 200a via the holder section 400 and the piston member 500. This allows flexibility in the layout of the apparatus, as compared to the case where the aspiration tip 100a is directly connected to a widely used aspiration pipet. Further, in the aspiration tip 100a of the second embodiment, the syringe section 110a is oriented in the vertical direction and the holder rear end portion 440 is disposed in the horizontal orientation of extending in the horizontal direction in the state of use. Even in this state, the aspiration tip 100a of the second embodiment can transmit a movement of the movable member 300a of the aspiration pipet 200a to the plunger 160a. Such aspiration pipet 200a makes it possible to improve the flexibility in the layout of other components of an aspiration apparatus, for example, so that the apparatus can be so designed as to be easily operated by a user. Hereinafter, an exemplary aspiration apparatus using the aspiration tip 100a of the second embodiment will be described.

<Aspiration Apparatus>

Figure 11:
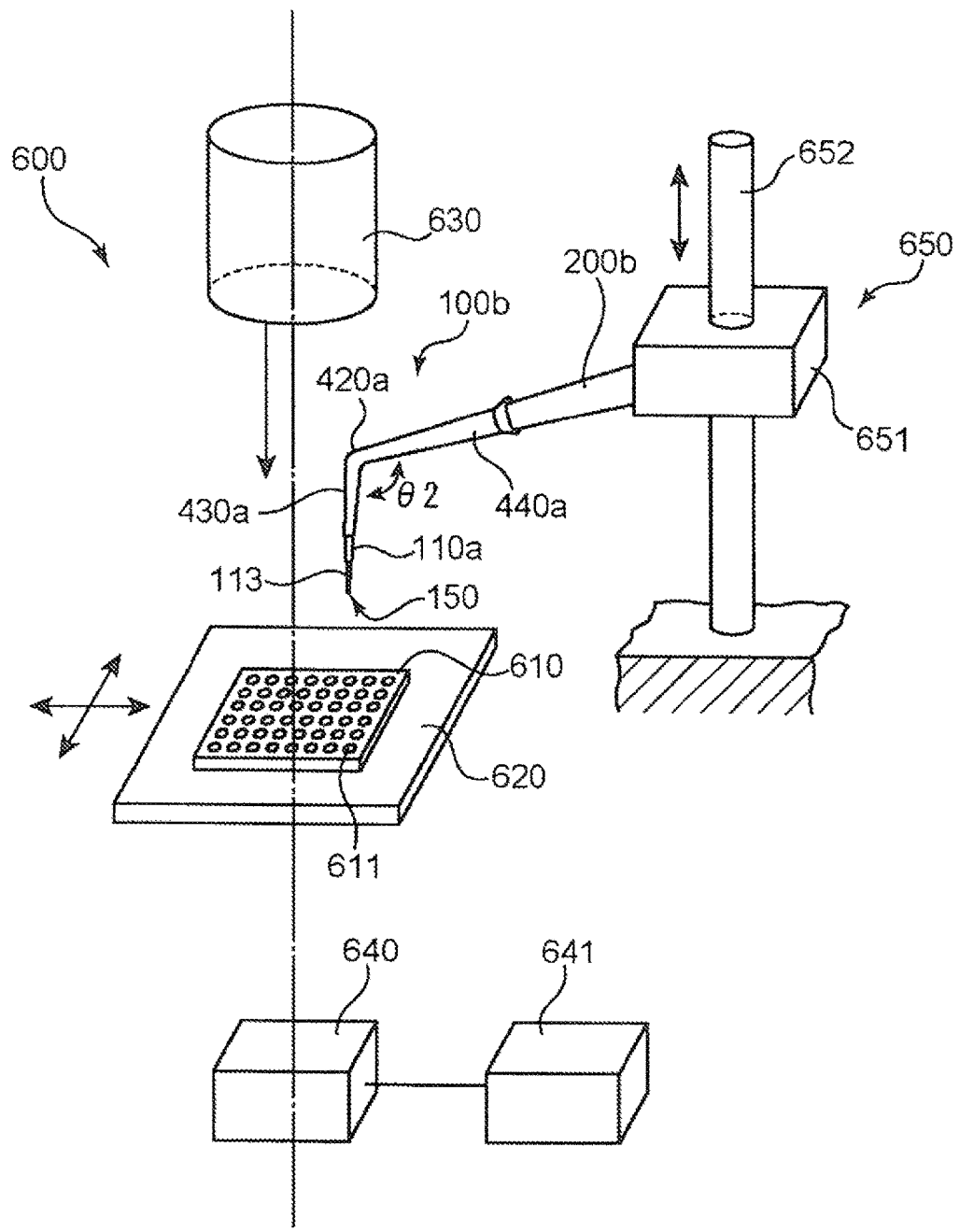
FIG. 11 is a schematic view illustrating a configuration of an aspiration apparatus using the aspiration tip according to the second embodiment of the present disclosure.

FIG. 11 is a schematic view illustrating a configuration of an aspiration apparatus 600 using an aspiration tip 100b. The aspiration apparatus 600 includes a stage 620 on which a culture well 610 is placed, the culture well 610 having holding holes 611 for holding cell aggregations to be aspirated, a condenser 630 (irradiator) spaced above the culture well 610 placed on the stage 620 for emitting beams of irradiation light to the cell aggregations held in the holding holes 611 from above, an imaging device 640 (observation device) for observing a cell aggregation held in a holding hole 611 from below, the aspiration tip 100b for aspirating a cell aggregation held in a holding hole 611, an aspiration pipet 200b for generating an aspiration force for the aspiration, and a moving device 650 (driver) for vertically moving the aspiration pipet 200b. The condenser 630 and the imaging device 640 constitute an illumination system and an imaging system of an inverted phase contrast microscope, respectively. Further, the aspiration tip 100b only differs from the above-described aspiration tip 100a (see FIG. 8) of the second embodiment in that the angle between a holder front end portion 430a and a holder rear end portion 440a at a bent portion 420a is set at 110 degrees. Accordingly, identical elements are denoted by the same reference numerals, and description thereof will be appropriately omitted.

The culture well 610 has a flat and a substantially cuboid shape with a top surface and a bottom surface. The holding holes 611 recessed downward from the top surface are arranged in a matrix with eight columns and six rows.

The culture well 610 is not limited to a particular shape. The culture well 610 is preferred to have a flat shape in terms of allowing the culture well 610 to be easily placed on the stage 620 described later, and facilitating the adjustment of the focus of an optical lens system included in the imaging device 640 at the time of observation of a cell aggregation held in a holding hole 611.

The width of the culture well 610 is not particularly limited, and only needs to be sufficient to allow placement of the culture well 610 on the stage 620. In this embodiment, the substantially cuboid culture well 610 having a bottom surface of 8.6 cm by 12.8 cm is placed on the stage 620 having a horizontal substantially rectangular top surface of 15 cm by 36 cm.

The material of the culture well 610 is not limited to a particular kind, but it is preferred to use a translucent material in terms of allowing the shape of a cell aggregation to be easily seen. The translucent material is not limited to a particular one, but it is preferred to use a thermoplastic resin, a thermosetting resin, a photo-curing resin, for example. More specifically, examples of the translucent material include a polyethylene resin, a polyethylene naphthalate resin, a polypropylene resin, a polyimide resin, a polyvinyl chloride resin, a cycloolefin copolymer, a norbornene-containing resin, a polyether sulfone resin, a polyethylene naphthalate resin, a cellophane, an aromatic polyamide resin, a (meta) acrylic resin such as poly(meta)methyl acrylate, a styrene resin such as a polystyrene or a styrene-acrylonitrile copolymer, a polycarbonate resin, a polyester resin, a phenoxy resin, a butyral resin, a polyvinyl alcohol, a cellulose-based resin such as ethyl cellulose, cellulose acetate, or cellulose acetate butyrate, an epoxy resin, a phenol resin, a silicone resin, and a polylactic acid. Further, it is preferred to use an inorganic material such as a solution obtained through hydrolysis and polymerization of a solution containing a metal alkoxide, a ceramic precursor polymer, and a metal alkoxide by a sol-gel process, or a solidified inorganic material including the above-mentioned combination such as an inorganic material (e.g. polydimethylsiloxane) containing a siloxane bond, or glass. It is possible to use a wide variety of glasses, such as a soda glass, a quartz, a borosilicate glass, a Pyrex (registered trademark) glass, a low melting glass, a photosensitive glass, and other optical glasses of various reflective indices and Abbe numbers.

The number of holding holes 611 is not particularly limited. One holding hole 611 may be formed or a plurality of holding holes 611 may be arranged in the culture well 610. In the case that a plurality of holding holes 611 are arranged, they are preferred to be arranged in a matrix. Such arrangement of the plurality of holding holes 611 would allow a plurality of cell aggregations to be simultaneously held in the respective holding holes 611, which in turn would improve the working efficiency.

The size of the holding hole 611 (diameter of the opening) is not particularly limited, and only needs to be sufficient to hold at least a part of a cell aggregation to be collected. The depth of the holding hole 611 is not particularly limited, and only needs to be sufficient to hold a cell aggregation. This embodiment illustrates the holding holes 611 each having a diameter of 9 mm and a depth of 11 mm.

The stage 620 is in the form of a horizontal flat plate-like stand including a rectangular holder (not shown) holding the culture well 610. The stage 620 includes a position adjustment mechanism (not shown) for moving the culture well 610 leftward and rightward and from side to side manually or automatically. The position adjustment mechanism adjusts the position of the culture well 610 placed on the stage 620 so that the condenser 630 described later is located above, and the imaging device 640 is located below the holding holes 611 holding cell aggregations to be aspirated. This allows beams of irradiation light emitted from the condenser 630 to fall on the holding holes 611 holding the cell aggregations to be aspirated from above and then enter the imaging device 640 located below.

The condenser 630 (irradiation device) is spaced above the culture well 610 placed on the stage 620 and is provided for irradiating the cell aggregations held in the holding holes 611 with beams of irradiation light from above. The condenser 630 includes a housing substantially in the form of a cylinder, and an unillustrated light source (halogen lamp (6V30 W)), a collector lens, a ring slit, an aperture stop, and a condenser lens that are placed in the housing. The light source is not limited to a particular type, and a tungsten lamp, a mercury lamp, a xenon lamp, a light emitting diode (LED) can be used other than the halogen lamp, for example. The ring slit is a baffle formed with an annular opening and is mounted at a position corresponding to the aperture stop of the condenser 630. The beams of irradiation light emitted from the light source of the condenser 630 passes through the collector lens, the opening of the ring slit, the aperture stop, and the condenser lens before falling on the cell aggregations held in the holding holes 611 and then enter the imaging device 640.

The imaging device 640 (observation device) is disposed below the culture well 610 placed on the stage 620 and is provided for observing a cell aggregation held in a holding hole 611 from below. The imaging device 640 includes an unillustrated phase contrast objective lens, an iris (lens optical system) for the objective lens, a phase plate, a field stop of an ocular, the ocular, a CCD (Charging Coupled Device) image sensor, an image processing unit, and a display device 641. The phase plate is in the form of a ring-shaped semitransparent plate, and weakens the intensity of light passing therethrough and delays the phase of the light by a quarter of a wavelength. The CCD image sensor converts an optical image formed on a light receiving surface into an electrical image data signal. The image processing unit performs image processing such as gamma correction and shading correction on image data as necessary. The display device 641 displays the image data having been subjected to the image processing. A user observes the image displayed on the image device 641. Beams of irradiation light that have been diffracted by a cell aggregation enter the phase contrast objective lens to form an image. At this time, most of the beams of irradiation light pass outside the phase plate, so that the phase of the light remains delayed by a quarter of a wavelength. The direct beams of light and the diffracted beams of light have the same phase and intensify each other by interference. This allows the cell aggregation to be observed in bright light.

In this embodiment, the components of the condenser 630 and the imaging device 640 are so arranged as to provide a Koehler illumination system. In other words, regarding the irradiation light, the light source, the aperture stop, and the exit stop of the objective lens are each disposed at a conjugate point, and regarding the image of a sample, the field stop, a cell aggregation (sample), the field stop of the ocular, and the light receiving surface of the CCD image sensor are each disposed at a conjugate point. In the Koehler illumination system, an image of the light source is formed at the aperture stop and an image of the field stop is formed on the sample surface, so that the sample cell aggregation is illuminated uniformly and brightly. Further, because the field stop and the aperture stop can be caused to function independently, it is possible to adjust the amount and range of light on the sample surface.

The aspiration pipet 200b is in the form of a tubular member and is capable of generating an aspiration force. The aspiration tip 100b is connected to the aspiration pipet 200b, the aspiration pipet 100b being provided for aspirating a cell aggregation held in a holding hole 611. When the aspiration pipet 200b generates an aspiration force, an aspiration force is generated in the tubular passage of the aspiration tip 100b, so that a cell aggregation is aspirated and collected through the aspiration opening 150. The aspiration pipet 200b is connected to the moving device 650 described later for use, and is driven to vertically move by the moving device 650.

As described above, in the state of use of the aspiration tip 100b, the syringe section 110a and the holder front end portion 430a are substantially oriented in the vertical direction and the holder rear end portion 440a is disposed in the horizontal orientation of extending in the horizontal direction. Accordingly, in the case that the above-described components of the condenser 630 and the imaging device 640 are so arranged as to provide the Koehler illumination system, it is possible to locate the syringe section 110a and the holder front end portion 430a of the aspiration tip 100b between the condenser 630 and the culture well 610 while maintaining the arrangement. Consequently, it is possible to locate the moving device 650 obliquely above the culture well 610, i.e. at the position where the moving device 650 does not interrupt the beams of irradiation light emitted from the condenser 630, while locating the syringe section 110a and the holder front end portion 430a of the aspiration tip 100b in the space between the condenser 630 and the culture well 610. The way to introduce the aspiration tip 100b into the space between the condenser 630 and the culture well 610 is not limited to a particular one and, for example, a way of moving the stage 620 forward and backward and from side to side can be adopted.

The moving device 650 allows the aspiration pipet 200b to connect therewith in a horizontal orientation, and is provided for vertically moving the connected aspiration pipet 200b while maintaining the horizontal orientation of the aspiration pipet 200b, the moving device 650 being disposed obliquely above the stage 620. The moving device 650 includes a main body section 651 connecting with the aspiration pipet 200b, and a guide section 652 along which the main body section 651 travels. The main body section 651 is in the form of a substantially cuboid housing and includes, in the housing, a motor (not shown) for vertically moving the main body section 651 to thereby vertically move the aspiration pipet 200b, a controller (not shown) for controlling the motor, and a syringe pump (not shown) for moving a movable member (not shown) of the aspiration pipet 200b. A connection port (not shown) connecting with the aspiration pipet 200b is formed in an outer portion of the housing of the main body section 651, the connection port serving as an aspiration opening in which an aspiration force is generated by the syringe pump. The guide section 652 is provided with a linear gear (rack), and the main body section 651 is provided with a circular gear (pinion). The motor that is controlled by the controller is driven to cause the main body section 651 to travel along the guide section 652. The motor can not only vertically move the main body section 651 but also move the main body section 651 forward and backward and from side to side to bring the aspiration opening 150 of the aspiration tip 100b within the depth of field of the objective lens of the imaging device 640 to allow calibration of the aspiration apparatus 600. The calibration is performed as appropriate, such as when the aspiration tip 100b is replaced or when the apparatus is started up.

A downward movement of the main body section 651 allows the syringe section 110a of the aspiration tip to be inserted downward in a holding hole 611 holding a cell aggregation to bring the aspiration opening 150 close to the cell aggregation. The position of the cell aggregation and the position of the aspiration opening 150 are displayed on the display device 641 of the imaging device 640, which makes it possible to bring the aspiration opening 150 close to the cell aggregation accurately while monitoring the position of the aspiration opening 150. The beams of irradiation light emitted from the condenser 630 is interrupted only by the syringe section 110a and the holder front end portion 430a, which allows the cell aggregation to be observed under sufficient irradiation light. Thereafter, the aspiration pipet 200b generates an aspiration force in the tubular passage of the aspiration tip 100b to aspirate and collect the cell aggregation into the tubular passage. At this time, the display device 641 displays the state (presence or absence of the cell aggregation) of the holding hole 611, so that it is possible to easily determine whether the collection has succeeded. After the display device 641 determines that no cell aggregation is present in the holding hole 611, the main body section 651 is moved upward to thereby move the leading end of the syringe section 110a upward, whereby the syringe leading end portion 113 including the aspiration opening 150 is raised from the holding hole 611. The cell aggregation having been collected into the tubular passage is discharged to a collection plate (not shown) adjacent to the culture well 610 on the stage 620. Further, the imaging device 640 is moved forward and backward and from side to side appropriately to observe the cell aggregation that has been discharged in the collection plate. Further, the objective lens of the imaging device 640 is moved in the vertical direction appropriately to capture the cell aggregation having been discharged in the collection plate within the depth of field to focus the objective lens on the cell aggregation.

As described above, according to the aspiration apparatus 600 of this embodiment, the holder section 400 of the aspiration tip 100b includes the bent portion 420a having a substantially L-shape. This makes it possible to locate, by the moving device 650, the syringe section 110a almost immediately above a holding hole 611 so as to allow the syringe section 110a to be inserted into the holding hole 611 in a substantially vertical direction. Therefore, the moving device 650 can move the syringe section 110a in the vertical direction to thereby bring the aspiration opening 150 close to a cell aggregation in the vertical direction. At this time, the holder rear end portion 440a of the aspiration tip 100b is disposed in the horizontal orientation of extending in the horizontal direction from the space between the condenser 630 and the culture well 610. This makes it possible to connect the aspiration tip 100b to the aspiration pipet 200b that is disposed similarly in the horizontal orientation and connect the aspiration pipet 200b to the moving device 650, to thereby locate the moving device 650 at a position where the moving device 650 does not interrupt the beams of irradiation light emitted from the condenser 630 (e.g. obliquely above the stage 620), and not at a position where the moving device 650 interrupts the beams of irradiation light emitted from the condenser 630. Consequently, the cell aggregation is observed with the imaging device 640 under sufficient irradiation light. Therefore, the aspiration apparatus 600 including the aspiration tip 100b of this embodiment makes it possible to move the syringe section 110a downward to accurately bring the aspiration opening 150 close to the cell aggregation to collect the cell aggregation by the moving device 650 that is disposed at the position where the moving device 650 does not interrupt the beams of irradiation light emitted from the condenser 630, while observing the cell aggregation with the imaging device 640 under sufficient irradiation light.

The embodiments of the present disclosure have been described. The present disclosure is not limited to the above-described embodiments and, for example, the following modified embodiments may be adopted.

(1) In the above-described embodiments, the object that is aspirated by the aspiration tip is illustrated by a cell aggregation. Alternatively, the present disclosure may be used for liquid or a material held in liquid. The liquid is not limited to a particular kind, and a liquid having a high viscosity such as Matrigel (manufactured by BD Biosciences), Cellmatrix (manufactured by Nitta Gelatin Inc.) or collagen may be used. Further, the object that is held in liquid may be a colony of an iPS cell or an ES cell colony, a spheroid, an organoid, or a single cell, other than a cell aggregation. Regardless of which one of them is the object, the aspiration tip of the present disclosure is capable of eliminating the influence of air at the time of the aspiration and the discharge, so that the aspiration speed and the discharge speed are unlikely to decrease and therefore high working efficiency is achieved, as described above. Further, because no air intervenes both in the aspiration and in the discharge, the amount of the object that is aspirated is equal to the volume of the internal area of the syringe section that is defined as a result of retraction of the plunger. The object that has been aspirated into this internal area is then completely discharged. Therefore, the aspiration tip of the present disclosure is likely to allow aspiration and discharge of an accurate amount of an object. Further, at the time of the discharge, the plunger moves with the outer peripheral surface coming in contact with the inner wall surface of the syringe section to cause the plunger leading end portion to protrude from the aspiration opening. Therefore, the object is likely to be completely discharged without remaining on the inner wall surface or around the aspiration opening.

The present disclosure is preferably used for a biological cell, and more preferably, a biological cell aggregation. Specifically, in the case of use of the conventional aspiration tip, air intervenes when a cell is aspirated and discharged, so that the cell is liable to remain on the inner wall surface of the tubular passage or around the aspiration opening. However, in the aspiration tip of the present disclosure, air is discharged from the tubular passage of the syringe section by the plunger before the aspiration. Further, no air intervenes both in the aspiration and in the discharge because, in the aspiration, the plunger leading end portion is retracted in the syringe section and a cell is aspirated into the tubular passage from which the air has been discharged. Therefore, the cell is likely to be completely discharged without remaining on the inner wall surface or around the aspiration opening in the aspiration. As a result, the cell is measured accurately to yield highly reliable results in various experiments or the like.

Experimental results using a biological cell aggregation are considered as more important than experimental results using a single cell in the fields of regenerative medicine and development of pharmaceutical products such as anticancer drugs, because a biologically similar environment reflecting interactions between cells is reconstructed in the cell aggregation, which makes it possible to obtain results reflecting the function of each cell and bring experimental conditions into closer conformity to the environment in a living body. Specific examples of the cell aggregation include a BxPC-3 (human pancreatic adenocarcinoma cells), embryonic stem cells (ES cells), and induced pluripotent stem cells (iPS cells). In general, such a cell aggregation consists of several to hundreds of thousands of cells that are aggregated. In the aspiration tip of the present disclosure, air is discharged from the tubular passage of the syringe section by the plunger before the aspiration. Further, no air intervenes both in the aspiration and in the discharge because, in the aspiration, the plunger leading end portion is retracted in the syringe section and a cell aggregation is aspirated into the tubular passage from which the air has been discharged. Therefore, the cell aggregation is likely to be completely discharged without remaining on the inner wall surface or around the aspiration opening in the aspiration. As a result, the cell aggregation is measured accurately to yield highly reliable results in the fields of bio-related technology and medicine (including the fields of regenerative medicine and development of pharmaceutical products such as anticancer drugs).

(2) The above-described embodiments illustrate the case where a cell aggregation is held in cell culture solution. Alternatively, in an aspiration apparatus using the aspiration tip of the present disclosure, any liquid that does not deteriorate the properties of a cell aggregation can be appropriately used as the liquid for holding the cell aggregation. Representative examples of such liquid include a basal medium, a synthetic medium, Eagle's medium, RPMI medium, Fischer's medium, Ham's medium, MCDB medium, a blood serum medium, glycerol that is added before cryopreservation, a cell freezing solution such as Cell Banker (manufactured by JUJI FIELD Inc.), formalin, a reagent for fluorescent staining, antibodies, purified water, and a physiological salt solution. Further, it is possible to use a culture preservation solution suitable for a cell aggregation. For example, in the case that the cell aggregation consists of BxPC-3 (human pancreatic adenocarcinoma cells), it is possible to use RPMI-164 medium which is mixed with 10% of FBS (Fetal Bovine Serum) and, as necessary, added with antibiotics and a supplement such as sodium pyruvate.

(3) The above-described embodiments illustrate the case where the syringe large diameter part and the syringe main body portion are connected by the syringe connecting part, and the plunger large diameter part and the plunger connecting part are connected by the plunger connecting part. Alternatively, the aspiration tip of the present disclosure may be configured without the syringe connecting part and the plunger connecting part. In the case where the syringe connecting part is omitted, the syringe large diameter part and the syringe main body portion are directly connected. In this case, the tubular passage may be made to diametrically increase in the syringe large diameter part and to be formed with the contacting part. Further, in the case where the plunger connecting part is omitted, the plunger large diameter part and the plunger main body portion are directly connected. In this case, the connecting portion of the plunger main body portion and the plunger large diameter part functions as the plunger step part. The plunger step part may be configured to come into contact with the contacting part formed in the syringe large diameter part when the plunger moves a maximum distance in the discharge direction before the aspiration of, and at the time of the discharge of an object.

(4) The above-described embodiments illustrate the case where the movement of the plunger is restricted by the two contacting mechanisms when the plunger moves the maximum distance in the discharge direction before the aspiration of, and at the time of the discharge of an object. Specifically, the above-described embodiments illustrate the case where the movement of the plunger is restricted by the contacting mechanism in which the outer peripheral surface of the plunger connecting part comes into contact with the inner wall surface of the tubular passage portion of the syringe connecting part, and the contacting mechanism in which the plunger step part comes into contact with the bulging part formed on the inner wall surface of the syringe connecting part. Alternatively, the present disclosure may be configured to use one of these contacting mechanisms or without these contacting mechanisms.

(5) The above-described embodiments illustrate the case where grooves are formed in one member (e.g. the inner wall surface of the syringe large diameter part) and ridges are formed in another member (e.g. the outer peripheral surface of the nozzle section of the aspiration pipet) to bring the two members into engagement with each other. Alternatively, the present disclosure may be so configured that the grooves and the ridges are formed in the inverse members or with no grooves and ridges. Further, instead of providing grooves and ridges, the present disclosure may be so configured that one member has a tapering peripheral surface to be fitted to another member as in a case that a widely used aspiration pipet is fitted to an aspiration pipet.

The above-described specific embodiments mainly include the disclosure having the following configurations.

An aspiration tip according to an aspect of the present disclosure comprises: a syringe section including an inner tubular passage defining an aspiration path for aspirating an object; and a plunger movable in the tubular passage while coming in contact with an inner wall surface of the tubular passage, wherein the syringe section includes an aspiration opening formed in a distal end of the tubular passage for aspirating the object, and the plunger includes a plunger leading end portion configured to protrude from the aspiration opening before the aspiration of the object and at the time of discharge of the object, and retract in the syringe section at the time of the aspiration of the object.

As described, an aspiration tip of the present disclosure includes a syringe section including an inner tubular passage defining an aspiration path for aspirating an object, and a plunger movable in the tubular passage while coming in contact with an inner wall surface of the tubular passage. Further, the plunger includes a plunger leading end portion configured to protrude from the aspiration opening before the aspiration of the object and at the time of discharge of the object, and retract in the syringe section at the time of the aspiration of the object. Therefore, air is discharged from the tubular passage of the syringe section by the plunger before the aspiration. Further, no air intervenes both in the aspiration and in the discharge because, in the aspiration, the plunger leading end portion is retracted in the syringe section and the object is aspirated into the tubular passage from which the air has been discharged. Therefore, the aspiration speed and the discharge speed are unlikely to decrease, which results in achievement of high working efficiency. Further, because no air intervenes both in the aspiration and in the discharge, the amount of the object that is aspirated is equal to the volume of the receiving area of the syringe section that is defined as a result of retraction of the plunger. The object that has been aspirated into this receiving area is then completely discharged. Therefore, the aspiration tip of the present disclosure is likely to allow aspiration and discharge of an accurate amount of an object. Further, at the time of the discharge, the plunger moves while coming in contact with the inner wall surface of the syringe section to cause the plunger leading end portion to protrude from the aspiration opening. Therefore, the object is likely to be completely discharged without remaining on the inner wall surface or around the aspiration opening. Further, because the aspirated object is completely discharged, even in the case that the aspiration tip is used repeatedly, sample contamination is unlikely to occur between the samples that have been successively taken. Further, when the object is observed with an observation device such as a microscope while the object is held in the aspiration tip, for example, no air exists in the tubular passage, which provides an improved observation accuracy.

In the above-described configuration, the syringe section is preferred to be made of a material having a higher rigidity than the plunger.

According to this configuration, the syringe section is made of a material having a higher rigidity than the plunger. Therefore, the syringe section is unlikely to shift due to a stress applied from the plunger when the plunger moves back and forth while coming in contact with the inner wall surface of the syringe section. Consequently, even in the case that a minute object such as a cell aggregation is aspirated, the aspiration can be performed while maintaining the relative positions of the cell aggregation and the aspiration opening. This improves the aspiration accuracy of the aspiration tip.

In the above-described configuration, it is preferred that the syringe section includes a syringe base end portion and a syringe main body portion; the syringe main body portion has a linear shape with one end connecting with the syringe base end portion and the other end opposite to the one end, the syringe main body portion having an outer periphery diametrically decreasing from the one end to the other end; the plunger includes a plunger base end portion and a plunger main body portion; the plunger base end portion is placed in the syringe base end portion; the plunger main body portion has one end connecting with the plunger base end portion and the other end opposite to the one end; the tubular passage is disposed in the syringe main body portion and is in the form of a cylinder having a constant inner diameter; and the plunger main body portion includes a first main body part in the form of a cylinder having a constant outer diameter, the first main body part being movable in the tubular passage of the plunger main body portion with a circumferential surface of the cylinder coming in contact with an inner wall surface of the syringe main body portion.

According to this configuration, the syringe main body portion has a linear shape with an outer periphery diametrically decreasing from one end to the other end. Therefore, even in the case that the object is held in a narrow space, the aspiration opening is easily brought close to the object. Further, the tubular passage is disposed in the syringe main body portion and is in the form of a cylinder having a constant inner diameter. Further, the plunger main body portion includes a first main body part in the form of a cylinder having a constant outer diameter, the first main body part being movable in the tubular passage with a circumferential surface of the cylinder coming in contact with an inner wall surface of the syringe main body portion. Therefore, when the plunger moves back and forth in the tubular passage, the cylindrical outer peripheral surface of the first main body part is likely to come into close contact with the inner wall surface of the syringe main body portion. Consequently, air is less likely to intervene between them at the time of the aspiration and at the time of the discharge. This allows the aspiration tip to aspirate and discharge the object efficiently and accurately.

In the above-described configuration, it is preferred that the syringe section further includes a syringe leading end portion having a first conical part and a second conical part joining the first conical part; the first conical part has one end connecting with the syringe main body portion and the other end opposite to the one end, the first conical part narrowing from the one end to the other at a first reduction rate; and the second conical part has one end connecting with the other end of the first conical part and the other end bearing the aspiration opening, the second conical part narrowing from the one end to the other end at a second reduction rate greater than the first reduction rate.

According to this configuration, the syringe section further includes a syringe leading end portion. The syringe leading end portion has a first conical part and a second conical part joining the first conical part. The first conical part has one end connecting with the syringe main body portion and the other end opposite to the one end, the first conical part narrowing from the one end to the other at a first reduction rate. The second conical part has one end connecting with the other end of the first conical part and the other end bearing the aspiration opening, the second conical part narrowing from the one end to the other end at a second reduction rate greater than the first reduction rate. Therefore, even in the case that the object is held in a narrow space such as a minute holding hole of a well (culture well), for example, the second conical part is easily allowed to go deep into the holding hole to bring the aspiration opening close to the object.

In the above-described configuration, it is preferred that the syringe base end portion includes a receiving part disposed on an inner wall surface of the syringe base end portion; the plunger base end portion includes a contacting part disposed on an outer peripheral surface of the plunger base end portion; and the contacting part comes to engage with the receiving part when the plunger leading end portion protrudes from the aspiration opening in the movement of the plunder in the tubular passage before the aspiration of the object and at the time of the discharge of the object.

According to this configuration, the syringe base end portion includes a receiving part disposed on an inner wall surface of the syringe base end portion, and the plunger base end portion includes a contacting part disposed on an outer peripheral surface of the plunger base end portion. The contacting part comes to engage with the receiving part when the plunger leading end portion protrudes from the aspiration opening in the movement of the plunger in the tubular passage before the aspiration of the object and at the time of the discharge of the object. Therefore, the plunger leading end portion protrudes from the aspiration opening only by a predetermined length sufficient to permit discharge of air and the object from the syringe section, and does not protrude excessively from the aspiration opening. This makes it possible to improve the working efficiency and prevent the protruding plunger leading end portion from being damaged.

According to the above-described configuration, it is preferred that the syringe base end portion includes a syringe large diameter part in the form of a cylinder, a syringe connecting part connecting the syringe large diameter part and the syringe main body portion, and the receiving part disposed on an inner wall surface of the syringe connecting part; the plunger base end portion includes a plunger large diameter part in the form of a cylinder and placed in the syringe large diameter part, a plunger connecting part connecting the plunger large diameter part and the plunger main body portion, and the contacting part defined by a plunger step part formed at a connecting position between the plunger large diameter part and the plunger connecting part; and the receiving part is defined by a bulging part on the inner wall surface of the syringe connecting part that bulges toward an axial center of the syringe connecting part.

According to this configuration, the contacting part is defined by a plunger step part that connects the plunger large diameter part and the plunger connecting part, and the receiving part is defined by a bulging part on the inner wall surface of the syringe connecting part that bulges toward an axial center of the syringe connecting part. This allows, when the plunger moves in a discharge direction before and at the time of the aspiration of the object, the plunger step part to come into contact with the bulging part to thereby stop the plunger from moving in the discharge direction. As a result, the plunger leading end portion protrudes from the aspiration opening only by the predetermined length sufficient to permit the discharge of the air and the object from the syringe section, and does not protrude excessively from the aspiration opening. This makes it possible to improve the working efficiency and prevent the protruding plunger leading end portion from being damaged.

In the above-described configuration, it is preferred that the syringe base end portion includes a syringe large diameter part in the form of a cylinder, a syringe connecting part connecting the syringe large diameter part and the syringe main body portion, and the receiving part disposed on an inner wall surface of the syringe connecting part; the plunger base end portion includes a plunger large diameter part in the form of a cylinder and placed in the syringe large diameter part, a plunger connecting part connecting the plunger large diameter part and the plunger main body portion, and the contacting part disposed on an outer peripheral surface of the plunger connecting part, a peripheral surface of the contacting part being in the form of a curved projection; and a peripheral surface of the receiving part is in the form of a curved recess for receiving the contacting part.

According to this configuration, the syringe base end portion includes the receiving part disposed on an inner wall surface of the syringe connecting part, and the plunger base end portion includes the contacting part disposed on an outer peripheral surface of the plunger connecting part. The contacting part is in the form of a curved surface, and the receiving part is in the form of such a curved surface as to come into contact with the contacting part. This allows, when the plunger moves in the discharge direction before the aspiration of, and at the time of the discharge of the object, the contacting part to come into contact with the receiving part to thereby stop the plunger from moving in the discharge direction. As a result, the plunger leading end portion protrudes from the aspiration opening only by the predetermined length sufficient to permit the discharge of the air and the object from the syringe section, and does not protrude excessively from the aspiration opening. This makes it possible to improve the working efficiency and prevent the protruding plunger leading end portion from being damaged.

In the above-described configuration, it is preferred that the syringe section has the other end opposite to the distal end bearing the aspiration opening; and the plunger has the other end opposite to the plunger leading end portion, the aspiration tip further comprising: a holder section attached to the other end of the syringe section and including an internal passage communicating with the tubular passage of the syringe section; and a piston member attached to the other end of the plunger and movable in the holder section.

According to the above-described configuration, the aspiration tip further includes: a holder section attached to the other end of the syringe section and including an internal passage communicating with the tubular passage of the syringe section; and a piston member attached to the other end of the plunger and movable in the holder section. This makes it possible to connect the syringe section and the plunger of the aspiration tip with an aspiration apparatus such as an aspiration pipet via the holder section and the piston member. This allows flexibility in the layout of the apparatus, as compared to the case where the aspiration tip is directly connected to a widely used aspiration pipet.

In the above-described configuration, it is preferred that the syringe section is substantially oriented in a vertical direction in the state of use; and the holder section includes a bent portion formed in an L-shape; a holder front end portion disposed in front of the bent portion and attached to the other end of the syringe section; and a holder rear end portion disposed behind the bent portion and in a horizontal orientation of extending in a horizontal direction.

According to this configuration, the syringe section is oriented in a substantially vertical direction in the state of use. Further, the holder section includes a bent portion formed in an L-shape; a holder front end portion disposed in front of the bent portion and attached to the other end of the syringe section; and a holder rear end portion disposed behind the bent portion and in a horizontal orientation of extending in a horizontal direction. Therefore, in the case that an observation device such as a microscope is disposed below a container holding an object, and an irradiator including a light source, such as a condenser, is disposed above the container, for example, it is possible to place the aspiration tip in the space between the container and the irradiator without interrupting the beams of irradiation light emitted from the irradiator on the object. Thus, use of such aspiration tip makes it possible to aspirate and discharge an object while observing the position, the shape, and the like of the object with a bright view by irradiating the object with beams of irradiation light from behind.

In the above-described configuration, the object is preferred to be a biological cell.

In the case of use of the conventional aspiration tip, air intervenes when a cell is aspirated and discharged, so that the cell is liable to remain on the inner wall surface of the tubular passage or around the aspiration opening. However, in the aspiration tip of the present disclosure, air is discharged from the tubular passage of the syringe section by the plunger before the aspiration. Further, no air intervenes both in the aspiration and in the discharge because, in the aspiration, the plunger leading end portion is retracted in the syringe section and a cell is aspirated into the tubular passage from which the air has been discharged. Therefore, the cell is likely to be completely discharged without remaining on the inner wall surface or around the aspiration opening in the discharge. As a result, the cell is measured accurately to yield highly reliable results in various experiments or the like.

In the above-described configuration, the object is preferred to be a biological cell aggregation.

Experimental results using a biological cell aggregation are considered as more important than experimental results using a single cell in the fields of regenerative medicine and development of pharmaceutical products such as anticancer drugs, because a biologically similar environment reflecting interactions between cells is reconstructed in the cell aggregation, which makes it possible to obtain results reflecting the function of each cell and bring experimental conditions into closer conformity to the environment in a living body. In the aspiration tip of the present disclosure, air is discharged from the tubular passage of the syringe section by the plunger before the aspiration. Further, no air intervenes both in the aspiration and in the discharge because, in the aspiration, the plunger leading end portion is retracted in the syringe section and a cell aggregation is aspirated into the tubular passage from which the air has been discharged. Therefore, the cell aggregation is likely to be completely discharged without remaining on the inner wall surface or around the aspiration opening in the discharge. As a result, the cell aggregation is measured accurately to yield highly reliable results in the fields of bio-related technology and medicine (including the fields of regenerative medicine and development of pharmaceutical products such as anticancer drugs).

The invention claimed is:

1. An aspiration tip, comprising:
a syringe section including an inner tubular passage defining an aspiration path for aspirating an object; and
a plunger movable in the tubular passage while coming in contact with an inner wall surface of the tubular passage, wherein
the syringe section includes an aspiration opening formed in a distal end of the tubular passage for aspirating the object, and
the plunger includes a plunger leading end portion configured to protrude from the aspiration opening at the time of starting an aspiration of the object and at the time of finishing a discharge of the object, and retract in the syringe section at the time of the aspiration of the object, wherein
the syringe section includes a syringe base end portion and a syringe main body portion;
the plunger includes a plunger base end portion and a plunger main body portion;
the syringe base end portion includes a receiving part disposed on an inner wall surface of the syringe base end portion;
the plunger base end portion includes a contacting part disposed on an outer peripheral surface of the plunger base end portion; and
the contacting part comes to engage with the receiving part when the plunger leading end portion protrudes from the aspiration opening in the movement of the plunger in the tubular passage at the time of starting the aspiration of the object and at the time of finishing the discharge of the object; wherein
the syringe base end portion includes:
a syringe large diameter part in the form of a cylinder,
a syringe connecting part connecting the syringe large diameter part and the syringe main body portion, and
the receiving part disposed on an inner wall surface of the syringe connecting part;
the plunger base end portion includes:
a plunger large diameter part in the form of a cylinder and placed in the syringe large diameter part,
a plunger connecting part connecting the plunger large diameter part and the plunger main body portion, and
the contacting part defined by a plunger step part formed at a connecting position between the plunger large diameter part and the plunger connecting part; and
the receiving part is defined by a bulging part on the inner wall surface of the syringe connecting part that bulges toward an axial center of the syringe connecting part; and wherein
the plunger connecting part directly attached to the plunger large diameter part and directly attached to the plunger main body portion, the plunger step part being a first contact surface formed on the one end;
the bulging part includes a second contact surface facing to the first contact surface; and
at the time of starting the aspiration of the object and at the time of finishing the discharge of the object, the plunger is located at a position where the first contact surface of the plunger comes into contact with the second contact surface of the bulging part so that the plunger leading end portion protrudes from the aspiration opening by a predetermined length.

2. The aspiration tip according to claim 1, wherein the syringe section is made of a material having a higher rigidity than the plunger.

3. The aspiration tip according to claim 1, wherein:
the syringe main body portion has a linear shape with one end connecting with the syringe base end portion and the other end opposite to the one end, the syringe main body portion having an outer periphery diametrically decreasing from the one end to the other end;
the plunger base end portion is placed in the syringe base end portion;
the plunger main body portion has one end connecting with the plunger base end portion and the other end opposite to the one end;
the tubular passage is disposed in the syringe main body portion and is in the form of a cylinder having a constant inner diameter; and
the plunger main body portion includes a first main body part in the form of a cylinder having a constant outer diameter, the first main body part being movable in the tubular passage of the plunger main body portion with a circumferential surface of the cylinder coming in contact with an inner wall surface of the syringe main body portion.

4. The aspiration tip according to claim 1, wherein:
the syringe section has the other end opposite to the distal end bearing the aspiration opening; and
the plunger has the other end opposite to the plunger leading end portion, the aspiration tip further comprising:
a holder section attached to the other end of the syringe section and including an internal passage communicating with the tubular passage of the syringe section; and
a piston member attached to the other end of the plunger and movable in the holder section.

5. The aspiration tip according to claim 4, wherein:
the syringe section is substantially oriented in a vertical direction; and
the holder section includes
a bent portion formed in an L-shape;
a first side of the bent portion being attached to the other end of the syringe section; and
a second side of the bent portion opposing to the first side extending in a horizontal direction.

6. The aspiration tip according to claim 1, wherein the object is a biological cell.

7. The aspiration tip according to claim 6, wherein the object is a biological cell aggregation.

8. The aspiration tip according to claim 1, wherein:
the second conical part includes a peripheral part with a tapered surface, and
the tapered surface is tapered at the range of 30 to 80 degrees with respect to a leading end surface of the syringe section where the aspiration opening is formed.

* * * * *